United States Patent
Earnhart et al.

(10) Patent No.: US 10,266,571 B2
(45) Date of Patent: *Apr. 23, 2019

(54) LYME DISEASE VACCINE

(71) Applicant: Virginia Commonwealth University, Richmond, VA (US)

(72) Inventors: Christopher G. Earnhart, Williamsburg, VA (US); Richard T. Marconi, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,162

(22) Filed: Nov. 25, 2016

(65) Prior Publication Data

US 2017/0114106 A1    Apr. 27, 2017

Related U.S. Application Data

(63) Continuation of application No. 14/243,476, filed on Apr. 2, 2014, now Pat. No. 9,534,021, which is a continuation of application No. 12/990,079, filed as application No. PCT/US2009/042513 on May 1, 2009, now abandoned.

(60) Provisional application No. 61/050,034, filed on May 2, 2008.

(51) Int. Cl.
| | | |
|---|---|---|
| *A61K 39/02* | (2006.01) | |
| *C07K 14/20* | (2006.01) | |
| *G01N 33/569* | (2006.01) | |
| *C07K 16/12* | (2006.01) | |
| *C07K 14/00* | (2006.01) | |
| *A61K 39/00* | (2006.01) | |

(52) U.S. Cl.
CPC .......... *C07K 14/20* (2013.01); *A61K 39/0225* (2013.01); *C07K 14/001* (2013.01); *C07K 16/1207* (2013.01); *G01N 33/56911* (2013.01); *A61K 39/00* (2013.01); *C07K 2319/00* (2013.01); *C07K 2319/21* (2013.01); *G01N 2333/20* (2013.01); *G01N 2469/20* (2013.01); *Y02A 50/401* (2018.01); *Y02A 50/57* (2018.01)

(58) Field of Classification Search
None
See application file for complete search history.

(56) References Cited

U.S. PATENT DOCUMENTS 5,571,718 A * 11/1996 Dunn .................. C07K 14/20
435/252.3

\* cited by examiner

*Primary Examiner* — Jana A Hines
*Assistant Examiner* — Khatol S Shahnan Shah
(74) *Attorney, Agent, or Firm* — W&C IP

(57) ABSTRACT

Antigenic polypeptides comprising linear immunodominant epitopes of *Borrelia* outer surface protein A (OspA) or *Borrelia* outer surface protein C (OspC) are useful as vaccines against Lyme disease, and as diagnostics for detecting *Borrelia* infections. The OspA and OspC antigenic polypeptides typically comprise a plurality of peptides representing epitope containing regions from multiple distinct phyletic groups. The antigenic polypeptides may also include epitopes from both *Borrelia* OspA and *Borrelia* OspC.

2 Claims, 7 Drawing Sheets
Specification includes a Sequence Listing.

Figure 1

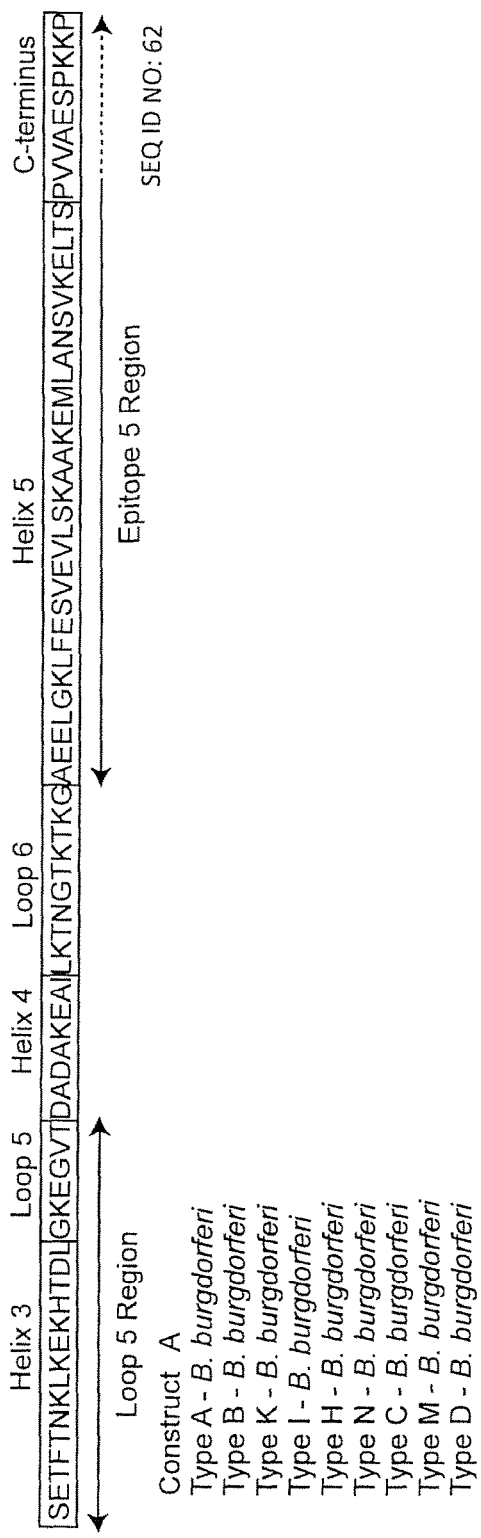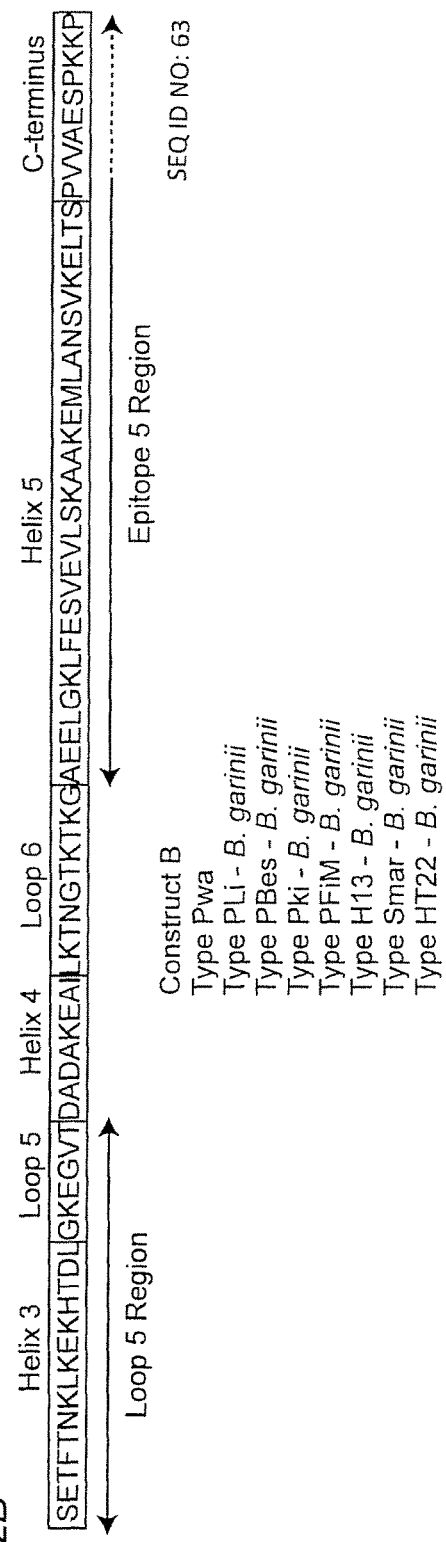
Figure 2A
Figure 2B

```
B31MI   17   CKQNVSSLDEKNSVSVDLPGEMKVLVSKEKNKDGKYDLIATVDKLELKGT
B331    17   .................N................................
LDP74   17   ..................................................

B31MI   67   SDKNNGSGVLEGVKADKSKVKLTISDDLGQTTLEVFKEDGKTLVSKKVTS
B331    67   ..................................................
LDP74   67   ..................................................

B31MI   117  KDKSSTEEKFNEKGEVSEKIITRADGTRLEYTGIKSDGSGKAKEVLKGYV
B331    117  ...........................E.....................
LDP74   117  ...........................E.....................

B31MI   167  LEGTLTAEKTTLVVKEGTVTLSKNISKSGEVSVELNDTDSSAATKKTAAW
B331    167  ..................................................
LDP74   167  ..................................................

B31MI   217  NSGTSTLTITVNSKKTKDLVFTKENTITVQQYDSNGTKLEGSAVEITKLD
B331    217  ..................................................
LDP74   217  ..................................................

B31MI   267  EIKNALK      SEQ ID NO: 74
B331    267  .......      SEQ ID NO: 75
LDP74   267  .......      SEQ ID NO: 76
```

Figure 5

LYME DISEASE VACCINE

BACKGROUND OF THE INVENTION

Field of the Invention

The invention generally relates to a vaccine and diagnostic for Lyme disease. In particular, the invention provides a Lyme disease vaccine and diagnostic that includes linear *Borrelia* outer surface protein A (OspA) epitopes and/or *Borrelia* outer surface protein C (OspC) epitopes, usually from multiple distinct phyletic groups.

Background of the Invention

Lyme disease is the most common arthropod-borne disease in North America and Europe, where in some areas up to 3% of the population is infected annually. Lyme disease is caused by the spirochetes *Borrelia burgdorferi, B. garinii* and *B. afzelii*. Transmission to mammals occurs through the bite of infected *Ixodes* ticks. Infection results in a multi-systemic inflammatory disease with early stage symptoms that may include erythema migrans, low-grade fever, arthralgia, myalgia, and headache. Late stage clinical manifestations can be severe and may include in part, arthritis and neurological complications. In addition, Lyme disease has significant socio-economic costs, manifested by reductions in outdoor recreational and social activities due to concerns about tick exposure.

The antigen used in first generation Lyme disease vaccines (e.g. LYMErix) was Outer surface protein A (OspA). OspA is only expressed by spirochetes in ticks, thus anti-OspA bactericidal activity occurs in the vector. However, a major drawback to the use of full-length OspA was the potential (whether real or perceived) for adverse events secondary to vaccination, such as the development of arthritis caused by immunological cross-reactivity with human proteins (e.g. LFA-1). This was a major factor in the withdrawal from the market of the original OspA-based LYMErix vaccine.

U.S. Pat. No. 6,248,562 (Jun. 19, 2001) to Dunn and Luft describes chimeric *Borrelia* proteins that can be used as immunodiagnostic reagents and vaccine immunogens against *Borrelia* infection.

U.S. Pat. Nos. 6,872,550 and 6,486,130 (Mar. 29, 2005, and Nov. 26, 2002, respectively) both to Livey, describe constructs for use a vaccines against Lyme disease.

U.S. Pat. No. 7,008,625 (Mar. 7, 2006) to Dattwyler et al. discloses chimeric *Borrelia* proteins that can be used as immunodiagnostic reagents and vaccine immunogens against *Borrelia* infection The publication "Recombinant Chimeric *Borrelia* Proteins for Diagnosis of Lyme Disease" (Maria J. C. Gomes-Solecki et al. 2000. J. Clin. Microbiol., 38: 2530-2535) also describes recombinant chimeric proteins.

Despite the above-referenced technologies, to date the prior art has failed to provide an efficacious vaccine for use in the prevention and/or treatment of Lyme disease.

SUMMARY OF THE INVENTION

In order to address prior art problems with Lyme disease vaccines, the OspA protein from *Borrelia burgdorferi* has been epitope mapped by assessing the reactivity of sera generated during murine infection with recombinant OspA subfragments. The epitope map demonstrated several linear epitope-containing regions of OspA. While conformational epitopes of OspA have been mapped and described, linear epitopes have not previously been reported for use in a vaccine. The use of one or more of these small, defined epitope-containing sequences in a polypeptide vaccine formulation allows the avoidance of specific regions of OspA that have been implicated in vaccine-mediated adverse events when full-length OspA is used. The inclusion of linear epitopes from a plurality of phyletic groups of *Borrelia* results in a vaccine that provides broad protection against infection over large geographical areas.

In addition, in other embodiments of the invention, one or more defined epitope-containing sequences from the *Borrelia* OspC protein have been used in vaccine formulations. Typically, epitopes or epitope-containing sequences from multiple phyletic groups are utilized.

Finally, the invention provides vaccine compositions which contain epitopes or epitope regions from both OspA and OspC.

It is an object of the invention 1. An isolated recombinant or synthetic peptide or polypeptide comprising at least one linear epitope from *Borrelia* outer surface protein A (OspA), said at least one linear epitope having an amino acid sequence selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26); and SEQ ID NO: 27.

In one embodiment, the at least one linear epitope is selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; and SEQ ID NO: 18.

The isolated recombinant or synthetic peptide or polypeptide may further comprise one or more amino acid sequences that are epitopes of *Borrelia* outer surface protein C (OspC), for example, one or more amino acid sequences that are epitopes of *Borrelia* OspC from an OspC loop 5 region or an OspC alpha helix 5 region, or both. The epitopes of OspC may be OspC types selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, and C. In some embodiments, the one or more amino acid sequences that are epitopes of *Borrelia* OspC are selected from the group of polypeptides having sequences as set forth in SEQ ID NOS: 65-73.

The invention also provides a method for eliciting an immune response against *Borrelia* in an individual in need thereof. The method comprises the step of administering to the individual an isolated recombinant or synthetic peptide or polypeptide comprising at least one linear epitope from *Borrelia* outer surface protein A (OspA). The at least one linear epitope having an amino acid sequence selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26); and SEQ ID NO: 27. In some embodiments, the at least one linear epitope has an amino acid sequence selected from the group consisting of SEQ ID NO: 1; SEQ ID NO: 2; SEQ ID NO: 3; SEQ ID NO:

4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; and SEQ ID NO: 18. According to some embodiments of the method, the isolated recombinant or synthetic peptide or polypeptide may further comprise one or more amino acid sequences that are epitopes of *Borrelia* outer surface protein C (OspC), for example, one or more amino acid sequences that are epitopes of *Borrelia* OspC from an OspC loop 5 region or an OspC alpha helix 5 region, or both. The epitopes of OspC may be OspC types selected from the group consisting of Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, and C. In some embodiments, the one or more amino acid sequences that are epitopes of *Borrelia* OspC are selected from the group of polypeptides having sequences as set forth in SEQ ID NOS: 65-73.

The invention further provides a method for ascertaining whether an individual has been exposed to or infected with *Borrelia*, or both. The method comprises the steps of 1) obtaining a biological sample from said individual; 2) exposing said biological sample to a recombinant or synthetic peptide or polypeptide comprising at least one linear epitope from *Borrelia* outer surface protein A (OspA), said at least one linear epitope having an amino acid sequence selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26); and SEQ ID NO: 27; and 3) determining whether antibodies in the biological sample bind to the recombinant or synthetic peptide or polypeptide, wherein detection of antibody binding is indicative of prior exposure to or infection with *Borrelia*. In some embodiments of this method, the recombinant or synthetic peptide or polypeptide further comprises one or more epitopes of *Borrelia* outer surface protein C (OspC), such as those having sequences as set forth in SEQ ID NOS: 65-73.

The invention further provides antibodies to a recombinant or synthetic peptide or polypeptide comprising at least one linear epitope from *Borrelia* outer surface protein A (OspA) or outer surface protein C (OspC). The at least one linear epitope having an amino acid sequence selected from the group consisting of: SEQ ID NOS: 1-27 (for OspA) and SEQ ID NOS: 65-73 (for OspC). In some embodiments, the antibody is bactericidal for *Borrelia* spirochetes.

The invention further provides an isolated recombinant or synthetic peptide or polypeptide comprising one or more epitopes from *Borrelia* outer surface protein A (OspA), said one or more epitopes being from an antigenic region selected from the group consisting of: antigenic region 221-240, antigenic region 17-67, antigenic region 94-144, and antigenic region 119-169. The isolated recombinant or synthetic peptide or polypeptide may further comprising one or more epitopes of *Borrelia* outer surface protein C (OspC).

The invention also provides an isolated recombinant or synthetic peptide or polypeptide comprising at least one linear epitope from *Borrelia* outer surface protein C (OspC). The at least one linear epitope may have an amino acid sequence selected from the group consisting of: SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; and SEQ ID NO: 73. The isolated recombinant or synthetic peptide or polypeptide may, in some embodiments, further comprise one or more epitopes of *Borrelia* outer surface protein A (OspA).

BRIEF DESCRIPTION OF THE DRAWINGS

FIG. 1. Alignment of the epitope-containing region of OspC protein sequences from all OspC types defined in this study. All sequences within OspC types that differ by more than one amino acid are indicated by a representative sequence. Identity threshold for shading is 80%. Secondary structural alpha helices and loops (corresponding to the B31 structure) are shown below the alignment (Kumaran, D., S. Eswaramoorthy, B. J. Luft, S. Koide, J. J. Dunn, C. L. Lawson, and S. Swaminathan. 2001. Crystal structure of outer surface protein C (OspC) from the Lyme disease spirochete, *Borrelia burgdorferi*. EMBO J. 20:971-978).

FIG. 2A-C. General epitope locations for OspC constructs. A, Construct A (SEQ ID NO: 62); B, Construct B (SEQ ID NO: 63), C, Construct C (SEQ ID NO: 64).

FIG. 5. Western blot mapping of OspA demonstrates several linear epitopes. r-OspA subfragments were screened with sera from mice infected for 6 weeks with one of three *B. burgdorferi* strains. Secondary antibody detection was IgG-specific. While all mice generated an anti-OspA response, as demonstrated by the full length protein (17-273), only a subset recognized linear epitopes on the tested subfragments. Of those fragments recognized, the most frequently and strongly recognized epitope was localized between amino acids 221 and 240.

Figure 2C:
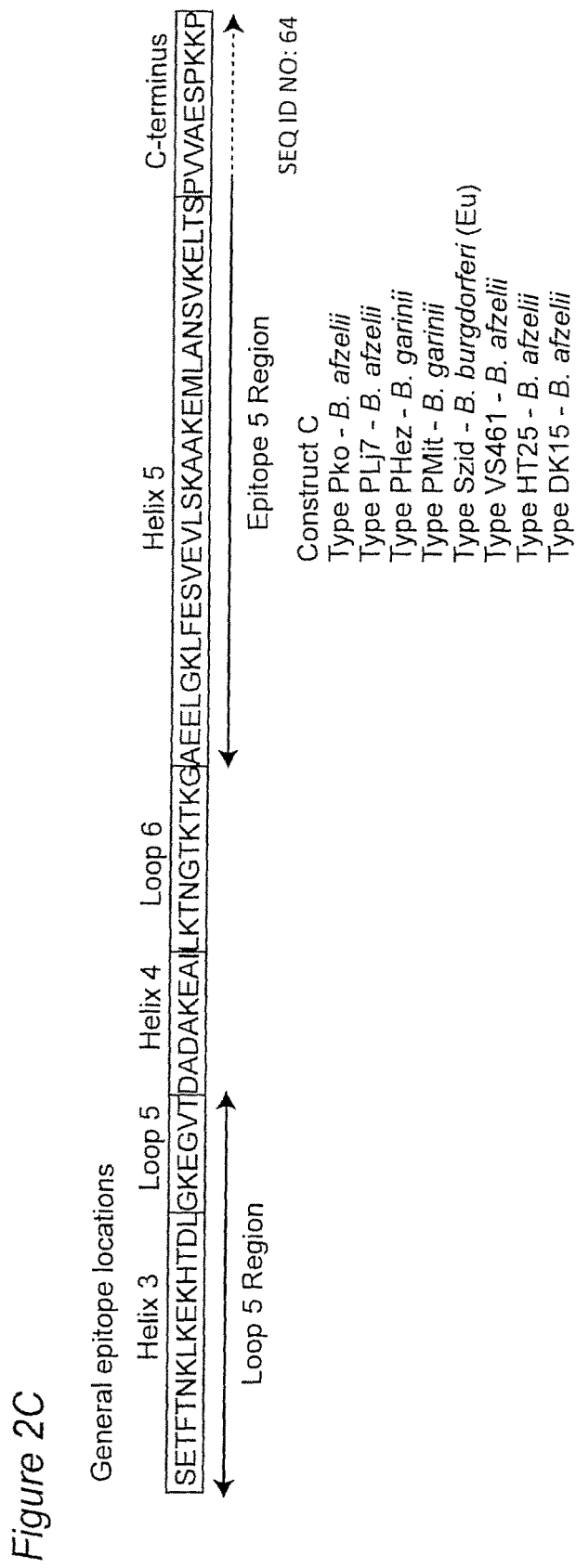

DETAILED DESCRIPTION OF THE
PREFERRED EMBODIMENTS OF THE
INVENTION

The present invention is based on the identification and characterization of linear peptide epitopes from *Borrelia* OspA protein. Identification of these epitopes has made possible the design and construction of chimeric (fusion) polypeptides that can be used as vaccines against Lyme disease, or as diagnostic tools. The polypeptides, which are generally isolated and/or purified, comprise at least one copy of an epitope from one of four classes of *Borrelia* OspA epitopes or antigenic regions. The four classes are organized based on the amino acid sequences numbering of OspA *Borrelia burgdorferi* strain 831M1, as follows:

Class I: Antigenic region 221-240;
Class II: Antigenic region 17-67;
Class III: Antigenic region 94-144; and
Class IV: Antigenic region 119-169.

The prototype Class I sequence is from *Borrelia burgdorferi* strain B31M1: Class I: STLTITVNSKKT-KDLVFTKE (SEQ ID NO: 1), which corresponds to residues 221-240 of OspA protein from *B. burgdorferi*. Additional corresponding or analogous type specific (i.e. phyletically related) exemplary Class I sequences that may be used in the practice of the invention include the following:

TABLE 1

Sequence variants at the 221-240 epitope containing region.

| Species | Accession number | SEQ ID NO: | Sequence |
|---|---|---|---|
| B. burgdorferi | NP045688.1 | 1 | STLTITVNSKKTKDLVFTKE |
| B. burgdorferi | CAB64758.1 | 2 | STLTIIVDSKNKTKLVFTKQ |
| B. burgdorferi | CAA56544.1 | 3 | STLTISKNRTKTKQLVFTKE |
| B. burgdorferi | CAA01705.1 | 4 | STLTISANSKKTKDLVFLTN |
| B. burgdorferi | CAR95557.1 | 5 | STLTITVNNKKTKALVFTKQ |
| B. burgdorferi and B. a.fzelii | ABF29588.1 CAA44092.1 | 6 | STLTISVNSKKTTQLVFTKQ |
| B. burgdorferi and B. garinii | AAB23810.1 AAT93773.1 | 7 | STLTISVNSKKTKNIVFTKE |
| B. burgdorferi and B. garinii | CAA82328.1 CAA56546.1 | 8 | STLTISVNSQKTKNLVFTKE |
| B. garinii | ACD02017.1 | 9 | NTLTVSADSKKIKDFVFLTD |
| B. garinii | ABF29554.1 | 10 | STLTISKNSQKTKQLVFTKE |
| B. garinii | AAO91930.1 | 11 | STLTISAKNKKTKDLVFTKQ |
| B. garinii | AAR96307.1 | 12 | STLKISKNSKKTKQLVFTKE |
| B. garinii | AAO91932.1 | 13 | STLTISAKSKKTKDLVFTKQ |
| B. garinii | ACD02015.1 | 14 | STLTISANNKKTKDLVFTKQ |
| B. garinii | AAR96306.1 | 15 | KTLTVSADSKKIKDFVFLTD |
| B. garinii | AAP94131.1 | 16 | STLTISAKNKKTTDLVFTKQ |
| B. garinii | ABF29567.1 | 17 | STLTISKNSRKTKQLVFTKE |
| B. garinii | AAP94130.1 | 18 | STLTISVNSRKTKNLVFTKE |

The prototype Class II sequence from *Borrelia burgdorferi* strain B31M1 is:

```
Class II:
                                         (SEQ ID NO: 19)
CKQNVSSLDEKNSVSVDLPGEMKVLVSKEKNKDGKYDLIATVDKLEL
KGTS,
``` which corresponds to residues 17-67 of OspA protein from *B. burgdorferi*.

The prototype Class III sequence from *Borrelia burgdorferi* strain B31M1 is:

```
Class III:
                                         (SEQ ID NO: 22)
LGQTTLEVFKEDGKTLVSKKVTSKDKSSTEEKFNEKGEVSEKIITRADGT
R,
``` which corresponds to residues 94-144 of OspA protein from *B. burgdorferi*.

The prototype Class IV sequence from *Borrelia burgdorferi* strain B31M1 is:

```
Class IV:
                                         (SEQ ID NO: 25)
KSSTEEKENEKGEVSEKIITRADGTRLEYTGIKSDGSGKAKEVLKGYVLE
G,
``` which corresponds to residues 119-169 of OspA protein from *B. burgdorferi*. Additional exemplary Class II, II and IV type-specific sequences that may be used in the practice of the invention include those depicted in Table 2. The sequences in Table 2 (SEQ ID NOS: 19-27) are exemplary, in that a phylogenetic analysis of *Borrelia* OspA at the indicated regions would generate additional potential sequences for use in the practice of the invention (i.e. additional sequences from other *Borrelia* species, strains or types).

TABLE 2

Example sequence variants for other epitope-containing sequences.

| Epitope region | Species | Accession number | SEQ ID NO: | Sequence |
|---|---|---|---|---|
| Amino acids 17-67 | B. burgdorferi | NP045688.1 | 19 | CKQNVSSLDEKNSVSVDLPGE MKVLVSKEKNKDGKYDLIAT VDKLELKGTS |
| Amino acids 17-67 | B. garinii | CAA56545.1 | 20 | CKQNVSSLDEKNSVSVDLPGG MTVLVSKEKDKDGKYSLEAT VDKLELKGTS |
| Amino acids 17-67 | B. afzelii | CAA59724.1 | 21 | CKQNVSSLDEKNSASVDLPGE MKVLVSKEKDKDGKYSLKAT VDKIELKGTS |

TABLE 2-continued

Example sequence variants for other epitope-containing sequences.

| Epitope region | Species | Accession number | SEQ ID NO: | Sequence |
|---|---|---|---|---|
| Amino acids 94-144 | *B. burgdorferi* | NP045688.1 | 22 | LGQTTLEVFKEDGKTLVSKKV TSKDKSSTEEKFNEKGEVSEKII TRADGTR |
| Amino acids 94-144 | *B. garinii* | CAA56545.1 | 23 | LSQTKFEIFKEDGKTLVSKKVT LKDKSSTEEKFNEKGETSEKTI VRANGTR |
| Amino acids 94-144 | *B. afzelii* | CAA59724.1 | 23 | LSKPTFELFKGDGETLVSRKVS SKDKTSTDEMFNEKGELSAKT MTRENGTK |
| Amino acids 119-169 | *B. burgdorferi* | NP045688.1 | 25 | KSSTEEKFNEKGEVSEKIITRA DGTRLEYTGIKSDGSGKAKEV LKGYVLEG |
| Amino acids 119-169 | *B. garinii* | CAA56545.1 | 26 | KSSTEEKFNEKGETSEKTIVRA NGTRLEYTDIKSDGSGKAKEV LKDFTLEG |
| Amino acids 119-169 | *B. afzelii* | CAA59724.1 | 27 | KTSTDEMFNEKGELSAKTMTR ENGTKLEYTEMKSDGTGKAK EVLKNFTLEG |

The use of one or more these linear epitopes in vaccine preparations advantageously avoids exposing the vaccine recipient to regions of OspA that have been implicated in putative adverse vaccine effects. The inclusion of a plurality of these linear sequences provides broad coverage against the development of Lyme disease for individuals over a broad geographical area. Or, when used as a diagnostic, the polypeptides of the invention enable detection of exposure to or infection with *Borrelia* of most important phyletic types over a broad geographical area. Further, the vaccine and/or diagnostic compositions can be "tuned" if desired, to represent one or more, but not all, geographical regions. For example, a vaccine or diagnostic developed for use in North America might contain only sequences derived from *B. burgdorferi*, as this is the only species associated with Lyme disease in that geographic area. In addition, in some embodiments of the invention, polypeptides containing one or more linear OspA epitopes or antigenic regions as described herein, may also include one or more OspC epitopes or antigenic regions, as described in detail below.

In order to facilitate the understanding of the present invention, the following definitions are provided:

Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide).

Epitope or B-cell Epitope: a specific chemical domain on an antigen that is recognized by a B-cell receptor, and which can be bound by secreted antibody. The term as used herein is interchangeable with "antigenic determinant".

Immunodominant epitope: The epitope on a molecule that induces the dominant, or most intense, immune response. The immunodominant epitope would elicit the greatest antibody titer during infection or immunization, as measured by, for example, the fraction of reactivity attributable to a certain antigen or epitope in an enzyme-linked immunosorbant assay as compared with the total responsiveness to an antigen set or entire protein.

Linear epitope: An epitope comprising a single, non-interrupted, contiguous chain of amino acids joined together by peptide bonds to form a peptide or polypeptide. Such an epitope can be described by its primary structure, i.e. the linear sequence of amino acids in the peptide chain. This is in contrast to conformational epitopes, which are comprised of at least some amino acids that are not part of an uninterrupted, linear sequence of amino acids, but which are brought into proximity to other residues in the epitope by secondary, tertiary and/or quaternary interactions of the protein. Residues in conformational epitopes may be located far from other resides in the epitope with respect to primary sequence, but may be spatially located near other residues in the conformational epitope due to protein folding.

Protein: A linear sequence of about 100 or more amino acids covalently joined by peptide bonds.

Polypeptide: A linear sequence of about 55 to about 100 amino acids covalently joined by peptide bonds.

Peptide: A linear sequence of about 55 or fewer amino acids covalently joined by peptide bonds.

Note: The terms "peptide", "polypeptide" and "protein" may be used interchangeably herein.

Chimeric or fusion peptide or polypeptide: a recombinant or synthetic peptide or polypeptide whose primary sequence comprises two or more linear amino acid sequences which do not occur together in a single molecule in nature. The two or more sequences may be, for example, a peptide (e.g. an epitope or antigenic region) and a linker sequence, or two or more peptides (which may be the same or different) which are either contiguous or separated by a linker sequences, etc.

Original or native or wild type sequence: The sequence of a peptide, polypeptide, protein or nucleic acid as found in nature.

Recombinant peptide, polypeptide, protein or nucleic acid: peptide, polypeptide, protein or nucleic acid that has been produced and/or manipulated using molecular biology techniques such as cloning, polymerase chain reaction (PCR), etc.

Synthetic peptide, polypeptide, protein or nucleic acid: peptide, polypeptide, protein or nucleic acid that has been produced using chemical synthesis procedures.

Type-specific: associated primarily with a single phyletic group.

Invasive infection: A protein is said to be "associated with invasive infection" if a Borrelia type bearing the protein has been isolated during human infection from locations other than the skin surrounding the initial inoculation by tick bite (e.g. from plasma, cerebrospinal fluid, etc.).

According to the invention, at least one amino acid sequence from Classes I-IV will be included in a peptide or polypeptide that is administered as a vaccine. In one embodiment of the invention, an antigenic chimeric (or fusion) polypeptide of the invention comprises one or more amino acid sequence from Class 1, such as those set forth in, for example, SEQ ID NOS: 1 and 2. Usually, one or more copies of two or more Class I sequences will be included, and each distinct sequence may be present in the polypeptide one or more time, i.e. multiple copies of one or more of the sequences set forth in, for example, SEQ ID NOS: 1 and 2 are included. For example, from about 1 to about 10 of the Class I sequences may be included, and for each separate sequence that is included, that sequence may be present in from about 2 to about 12 (e.g. 1, 2, 3, 4, 5, 6, 7, 8, 9, 10, 11 or 12) or more copies. Individual copies of the sequence may be separated by linker sequences (described below), although this need not always be the case, i.e. copies of the same or different antigenic regions may be contiguous in the polypeptide chain.

In other embodiments, one or more of the amino acid sequences set forth in or represented by the Class II or Class III or Class IV antigenic regions are included in the antigenic polypeptides of the invention. As is the case with the Class I epitopes, one or more of the peptides may be present in the antigenic polypeptide, and, for each distinct sequence that is present, multiple copies (e.g. from about 2 to about 12) may be included. Individual copies of the sequence may be separated by linker sequences, although this need not always be the case.

In yet other embodiments, mixtures of one or more copies of one or more Class I, Class II, Class III and/or Class IV antigenic regions are present in the antigenic polypeptides of the invention. In other words, the polypeptide includes a mixture antigenic regions from any of the four classes. Each of the sequences that is included may be present in one copy or, more frequently, as multiple copies. In this type of construct, the individual sequences may be present in any order. For example, one segment or section of the polypeptide may include multiple copies of e.g. SEQ ID NO: 1, while another section of the same polypeptide includes multiple copies of e.g. SEQ ID NO: 2, and so on. Alternatively, the sequences of e.g. SEQ ID NO: 1 and e.g. SEQ ID NO: 2 may alternate along the polypeptide chain so that the sequences are, in effect, interspersed amongst each other within the primary sequence of the polypeptide.

Other antigenic sequences of interest are those from other Borrelia proteins such as OspC. The invention thus provides chimeric polypeptides or proteins that comprise, one or more epitopes from OspC. Exemplary OspC epitopes include but are not limited to linear epitopes from the loop 5 and/or alpha helix 5 regions. The loop 5 region or domain of OspC is the region which includes residues that align with residues 131 to 159 of strain B31 (type A) OspC sequences (together with secondary structural elements such as a portion of alpha helix 3, loop 5, and alpha helix 4, as defined by Kumaran et al. The alpha helix 5 region/domain of OspC is the region which includes residues that align with amino acids 160 to 200 of the strain B31 (OspC type A) sequence and the C-terminal portion of the protein, amino acids 201-210 of the B31 sequence, as well as secondary structural elements including a portion of loop 6, alpha helix 5, and the unstructured C-terminal domain, as defined by Kumaran et al. (2001). According to the present invention, one or more peptides encompassing epitopes located within the primary linear sequence of OspC proteins from residues 131 to 200 (using the strain B31 type A OspC sequence as a reference for residue numbering) may be included in the immunogenic polypeptides of the invention, the polypeptides of the invention. Exemplary OspC regions from which epitopes may be selected are shown in FIG. 1, where the sequences corresponding to residues 131 to 200 of type A OspC from several Borrelia types are listed. One or more epitopes may be selected for inclusion, so that an entire 131-200 (or even 131-210 C-terminal) region encompassing several epitopes may be used. Alternatively, fragments of the 131-200 region may be employed, e.g. any contiguous sequence of from about 10 to about 50 amino acids. One or more of such contiguous sequences may be used in the practice of the invention, with preferable sequences being those corresponding to about amino acids 136 to 150 and about amino acids 168-203 of alpha helix 5.

In particular, the general epitope locations of suitable OspC-based sequences include Helix 3, Loop5, Loop6, Helix5 and a C-terminus sequence. Three exemplary constructs, denominated constructs A, B and C, are depicted schematically in FIGS. 2A-C(SEQ ID NOS: 62, 63 and 64). Constructs A, B and C differ in that the sequences contained therein are from different phyletic types. For example, as shown in FIG. 2A, Construct A contains sequences from Types A, B. K, 1, H, N, C, M and D of B. burgdorferi. In addition, for each of Constructs A, B and C, various versions or variations have been developed. The versions differ, for example, by the inclusion or exclusion of an intervening Helix-4/Loop6 sequence, by the order of the individual epitopes, and by other exclusions and or additions, etc. Exemplary variations of Constructs A, B and C are shown in Table 3.

TABLE 3

| Construct | Number of amino acids | Molecular weight | Theoretical pI | SEQ ID NO: |
|---|---|---|---|---|
| Construct A, version 1 | 569 | 60657.2 | 6.35 | 65 |

Sequence

```
SETFTNKLKEKHTDLGKEGVTDADAKEAILKTNGTKTKGAEELGKLFESVEVLSKAAKEM
<---------------------------Type A------------------------

LANSVKELTSSEEFSTKLKDNHAQLGIQGVTDENAKKAILKANAAGKDKGVEELEKLSGS
----------><----------------------Type B-------------------

LESLSSEDFTKKLEGEHAQLGIENVTDENAKKAILITDAAKDKGAAELEKLFKAVENLAA
----><--------------------Type K------------------------><

KLKGEHTDLGKEGVTDDNAKKAILKTNNDKTKGADELEKLFESVKNLSKAAKEMLTNSSE
--------------------Type I------------------------------><-

KFAGKLKNEHASLGKKDATDDDAKKAILKTHGNTDKGAKELKDLSDSVESLVSDDFTKKL
--------------------Type H-----------------------><-------

QSSHAQLGVAGGATTDEEAKKAILRTNAIKDKGADELEKLFKSVESLAKAAQDALANSVN
--------------------Type N-------------------------

ELTSKKLKEKHTDLGKKDATDVHAKEAILKTNGTKDKGAAELEKLFESVENLAKAAKEML
---><----------------------Type C-------------------------

SNSNKAFTDKLKSSHAELGIANGAATDANAKAAILKTNGTKDKGAQELEKLFESVKNLSK
--><--------------------------Type M-----------------------

AAQETLNNSSESFTKKLSDNQAELGIENATDDNAKKAILKTHNAKDKGAEELVKLSESVA
---------><-------------------------Type D-------------

GLLKAAQAILANSVKELTSPVVAESPKKP
---------------------------->
```

| Construct B, version 1 | 503 | 53102.4 | 7.16 | 66 |
|---|---|---|---|---|

Sequence

```
SEKFTTKLKDSHAELGIQSVQDDNAKKAILKTHGTKDKGAKELEELFKSLESLSKAAQAA
<-------------------------------------PWa--------------------

LTNSVKELTNSDKFTKKLTDSHAQLGAVGGAINDDRAKEAILKTHGTNDKGAKELKELSE
----------><------------------------PLi----------------------

SVESLAKAAQAALANSSEAFTKKLKDSNAQLGMQNGAATDAHAKAAILKTDATKDGATE
---------------><--------------------------PBes--------------

LGELFKSVESLSKAAQEASVAFTSKLKSSNAQLGVANGNATDDDAKKAILKTNTPNDKGA
----------------><--------------------------Pki-----------

KELKELFESVESLAKAAQAALVNSVQELTNSEAFTNRLKGSHAQLGVAAATDDHAKEAIL
----------------------------><-----------------PFiM--------

KSNPTKDKGAKELKDLSESVESLAKAAQEALANSVKELTNSEAFTKKLKDNNAQLGIQNV
----------------------------------------><----------H13------

QDVEAKKAILKTNGDISKSEAFTNKLKEKHAELGVNGGDTTDDNAKAAIFKTHPTKDKGV
----------------><------------------Smar--------------------

EDLEKLSESVKSLLKAAQAALSNSAAFTKKLQDGHVDLGKTDVTDDNAKEAILKTNPTKT
----------------------><-------------------------HT22-------

KGATELEELFKSVEGLVKAAKEA
---------------------->
```

| Construct C version 1 | 512 | 54372.0 | 8.14 | 67 |
|---|---|---|---|---|

Sequence

```
SEEFTNKLKSGHADLGKQDATDDHAKAAILKTHATTDKGAKEFKDLFESVEGLLKAAQVA
<-------------------------------------Pko--------------------
```

TABLE 3-continued

| Construct | Number of amino acids | Molecular weight | Theoretical pI | SEQ ID NO: |
|---|---|---|---|---|

```
LTNSVKELTSKLKGGHAELGLAAATDENAKKAILKTNGTKDKGAEELEKLFKSVESLAKA
---------><-----------------------------PLj7---------------

AKESLTNSVKELTNTKLRDSHAELGIQNVQDDNAKRAILKTHGNKDKGAKELKELSESLE
-------------><-----------------PHez----------------------

KLSKAAQAALANSVQELTSSEAFTNKLKEKTQELAVAAGAATDIDAKKAILKTNRDKDLG
-----------------><--------------PMit--------------------

ADERGKLFKSVESLSKAAQEASANSVKELTSSEAFTDKLKNEHASLGKKDATDDDAKKAI
------------------------------><----------------Szid-------

LKTNVDKTKGADELIKLSGSLESLSKAAQAILANSEAFTKKLQDSNADLGKHNATDADSK
---------------------------------><--------------VS461------

EAILKTNGTKTKGAKELEELFKSVESLSKAAKEALSNSVKELTSSQDFINKLKGGHAELG
--------------------------------------------><--------------

LVAATDANAKAAILKTNGDKTKGADEFEKLFKSVEGLLKAAQEALTNSVKELTSSEAFTK
-------HT25---------------------------------------><-----

KLQDSNADLGKHDATDADAKKAILKTDATKDK
-----------DK15---------------->
```

| Construct A version 2 | 431 | 46088.0 | 5.85 | 68 |
|---|---|---|---|---|

Sequence

```
SETFTNKLKEKHTDLGKEGVTKGAEELGKLFESVEVLSKAAKEMLANSVKELTSSEEFST
<-------Lp A---------><---------------Hx A--------------><---

KLKDNHAQLGIQGVTKGVEELEKLSGSLESLSSEDFTKKLEGEHAQLGIENVTAAELEKL
---Lp B--------><------Hx B------><---------Lp K---------><---

FKAVENLAKAAKEMAKLKGEHTDLGKEGVTKGADELEKLFESVKNLSKAAKEMLTNSKES
--Hx K--------><------Lp I-----><------------Hx I----------><

EKFAGKLKNEHASLGKKDATKGAKELKDLSDSVESLVKASDDFTKKLQSSHAQLGVAGGA
-------Lp H---------><--------Hx H--------><---------Lp N-------

TTADELEKLFKSVESLAKAAQDALANSVNELTSKKLKEKHTDLGKKDATAAELEKLFESV
-><--------------Hx N---------------><------Lp C----------><----------

ENLAKAAKEMLSNSNKAFTDKLKSSHAELGIANGAATKGAQELEKLFESVKNLSKAAQET
-Hx C-----------><----------Lp M---------><------------Hx M-----

LNNSVKESESFTKKLSDNQAELGIENATKGAEELVKLSESVAGLLKAAQAILANSVKELT
-------><---------Lp D---------><------------------Hx D---------

SPVVAESPKKP
---------->
```

| Construct B version 2 | 381 | 39928.6 | 5.79 | 69 |
|---|---|---|---|---|

Sequence

```
SEKFTTKLKDSHAELGIQSVQDKGAKELEELFKSLESLSKAAQAALTNSVKELTNSDKFT
<-----Lp PWa-----><---------------Hx PWa----------------><----

KKLTDSHAQLGAVGGAINDKGAKELKELSESVESLAKAAQAALANSSEAFTKKLKDSNAQ
-----Lp Pli-------><------------Hx Pli-----------><-------Lp PBes

LGMQNGAATDKGATELGELFKSVESLSKAAQEASVAFTSKLKSSNAQLGVANGNATDKGA
---------><---------Hx PBes---------><----------Lp Pki------><---

KELKELFESVESLAKAAQAALVNSVQELTNSEAFTNRLKGSHAQLGVAAATDKGAKELKD
-------Hx Pki------------------><-------Lp PFim------><---------

LSESVESLAKAAQEALANSVKELTNSEAFTKKLKDNNAQLGIQNVQSEAFTNKLKEKHAE
---Hx PFim-----------------><-----Lp H13--------><-----Lp Smar---

LGVNGGDTTDKGVEDLEKLSESVKSLLKAAQAALSNSAAFTKKLQDGHVDLGKTDVTTKG
---------><-----------Hx Smar------------><-------Lp HT22------><--
```

TABLE 3-continued

| Construct | Number of amino acids | Molecular weight | Theoretical pI | SEQ ID NO: |
|---|---|---|---|---|
| ATELEELFKSVEGLVKAAKEA<br>------Hx HT22------> | | | | |
| Construct C version 2 | 383 | 40492.5 | 6.45 | 70 |

Sequence

```
SEEFTNKLKSGHADLGKQDATKGAKEFKDLFESVEGLLKAAQVALTNSVKELTSKLKGGH
<-----Lp PKo---------><---------Hx PKo----------------><---Lp

AELGLAAATKGAEELEKLFKSVESLAKAAKESLTNSVKELTNTKLRDSHAELGIQNVQKG
PLj7----><-------------Hx PLj7-----------><----Lp PHez---><-

AKELKELSESLEKLSKAAQAALANSVQELTSSEAFTNKLKEKTQELAVAAGAATLGADER
---------Hx PHez---------------><--------Lp PMit--------><-----

GKLFKSVESLSKAAQEASANSVKELTSSEAFTDKLKNEHASLGKKDATKGADELIKLSGS
------Hx PMit--------------><------Lp Szid------><-----------

LESLSKAAQAILANSEAFTKKLQDSNADLGKHNATKGAKELEELFKSVESLSKAAKEALS
Hx Szid------><------Lp VS461-----><--------------Hx VS461---

NSVKELTSSQDFINKLKGGHAELGLVAATKGADEFEKLFKSVEGLLKAAQEALTNSVKEL
--------><------Lp HT25-----><-------------Hx HT25-----------

TSSEAFTKKLQDSNADLGKHDAT
-><------Lp DK15------>
```

| Construct A version 3 | 432 | 46201.2 | 5.85 | 71 |
|---|---|---|---|---|

Sequence

```
SETFTNKLKEKHTDLGKEGVTKGAEELGKLFESVEVLSKAAKEMLANSVKELTSKGVEEL
<--------Lp A-------><--------------Hx A--------------><-----

EKLSGSLESLSNKAFTDKLKSSHAELGIANGAATKKLKEKHTDLGKKDATKGADELEKLF
--Hx B----><----------Lp M---------><-----Lp C------><-------

ESVKNLSKAAKEMLTNSKEIAAELEKLFKAVENLAKAAKEMAKLKGEHTDLGKEGVTSEE
----Hx I--------------><---------Hx K---------><------Lp I----->

FSTKLKDNHAQLGIQGVTKGAKELKDLSDSVESLVKAAAELEKLFESVENLAKAAKEMLS
<------Lp B--------><--------Hx H--------><-----------Hx C--------

NSSEKFAGKLKNEHASLGKKDATSEDFTKKLEGEHAQLGIENVTKGAQELEKLFESVKNL
-><---------Lp H--------><---------Lp K---------><---------Hx M-

SKAAQETLNNSVKEADELEKLFKSVESLAKAAQDALANSVNELTSSESFTKKLSDNQAEL
---------------><-------------Hx N----------------><--------Lp D---

GIENATSDDFTKKLQSSHAQLGVAGGATTKGAEELVKLSESVAGLLKAAQAILANSVKEL
------><--------Lp N---------><---------------------Hx D------

TSPVVAESPKKP
----------->
```

| Construct B version 3 | 382 | 40056.8 | 5.93 | 72 |
|---|---|---|---|---|

Sequence

```
SEAFTKKLKDSNAQLGMQNGAATDKGAKELEELFKSLESLSKAAQAALTNSVKELTNKDK
<----------Lp PBes----><--------------Hx PWa--------------><--

GAKELKELFESVESLAKAAQAALVNSVQELTNSEKETTKLKDSHAELGIQSVQSDKFTKK
---------Hx PKi----------------><-------Lp PWa--------><------

LTDSHAQLGAVGGAINDKGAKELKELSESVESLAKAAQAALANSDKGAKELKDLSESVES
-Lp Pli--------><---------Hx Pli-----------><-------------Hx

LAKAAQEALANSVKELTNSVAFTSKLKSSNAQLGVANGNATSEAFTKKLKDNNAQLGIQN
PFim-------------><------Lp PKi----------><-----Lp H13------
```

TABLE 3-continued

| Construct | Number of amino acids | Molecular weight | Theoretical pI | SEQ ID NO: |
|---|---|---|---|---|
| VQTKGATELEELFKSVEGLVKAAKEADKGVEDLEKLSESVKSLLKAAQAALSNSAAFTKK<br>-><-------Hx HT22------><---------Hx Smar--------><------<br><br>LQDGHVDLGKTDVTSEAFTNRLKGSHAQLGVAAATDKGATELGELFKSVESLSKAAQEAS<br>Lp HT22------><-----Lp PFim-------><-------Hx PBes--------><<br><br>EAFTNKLKEKHAELGVNGGDTT<br>-------Lp Smar------->  | | | | |
| Construct C version 3 | 383 | 40622.6 | 6.10 | 73 |

Sequence

SEEFTNKLKSGHADLGKQDATKGAKEFKDLFESVEGLLKAAQVALTNSVKELTSKEKGAE
<------Lp PKo-------><-------------Hx PKo-------------><-----

ELEKLFKSVESLAKAAKESLTNSVKELTNSEAFTDKLKNEHASLGKKDATTKLRDSHAEL
----Hx PLj7----------------><-----Lp Szid-------><-------Lp GIQNVQLGADERGKLFKSVESLSKAAQEASANSVKELTSKEKGAKELEELFKSVESLSKA
PHez-><------------Hx PMit-------------><----------Hx VS461-

AKEALSNSVKELTSSEAFTKKLQDSNADLGKHNATSEAFTKKLQDSNADLGKHDATKGAD
--------------><-------Lp VS461------><-------Lp DK15-----><---

EFEKLFKSVEGLLKAAQEALTNSVKELTSELKELSESLEKLSKAAQAALANSVQELTSSE
-------Hx HT25---------------><-----------Hx PHez---------><-

AFTNKLKEKTQELAVAAGAATKLKGGHAELGLAAATKGADELIKLSGSLESLSKAAQAIL
-----Lp PMit--------><----Lp PLj7---><---------Hx Szid-------

ANSQDFINKLKGGHAELGLVAAT
-><-----Lp H125------->

In some embodiments, at least two of the OspC epitopes included in the chimeric polypeptide are from different OspC types that are associated with invasive infection. For example, antigenic epitopes representing from about 2 to about 20, and preferably from about 6 to about 10, different OspC types are included in a chimeric protein. When used as a vaccine, such a multivalent (polyvalent) recombinant chimeric protein elicits broad protection against infection with Borrelia spirochetes expressing the OspC types that correspond to those in the chimeric protein, i.e. those Borrelia that are highly infective. While typically at least two of the epitopes are different from one another in primary sequence and originate from different OspC types, it is also possible to include multiple copies of a single type of OspC epitope in a chimera, or to include several sequences that are based on or derived from the original sequence of the same OspC type. While the total number of linear OspC epitopes in a chimera may vary somewhat, in general, the range will be from about 10 to about 20. In one embodiment of the invention, the immunodominant OspC epitopes are selected from OspC types Smar, PLi, H13, PFiM, SL10, PMit, PKi, Pbes, HT22, Pko, PLj7, VS461, DK15, HT25, A, 72a, F, E, M, D, U, I, L, H, Szid, PHez, PWa, B, K, N, C. Those of skill in the art will recognize that epitopes from many combinations of OspC types may be used, so long as the resulting chimera produces a suitable immune response and/or is effective as a vaccine in preventing Lyme disease. Examples of suitable combinations of OspC epitopes (which may optionally be combined with OspA epitopes of Classes I-IV) include but are not limited to: 1) E, N, I, C, A, B, K, D; 2) A, B, K, D, E, N, C; 3) I, C, A, B, K, D; and 4) C, A, B, K, D.

In some embodiments, both the OspC loop 5 and OspC alpha helix 5 regions will be included. For example, an "E, N, I, C, A, B, K, D" construct may contain both the loop 5 and helix 5 regions of each of OspC types E, N, I, C, A, B. K, and D. However, this need not be the case. For example, the loop 5 region of type A and the alpha helix 5 regions of E, N, I, C, B, K, and D may be included; or only the loop 5 region for each OspC type may be included; or only the alpha helix 5 region; or other combinations may be included (e.g. loop 5 region of types E, N, I, and C and the alpha helix 5 region of types A, B, K, and D. Many such combinations will occur to those of skill in the art, and all such variations are intended to be encompassed herein.

In other embodiments of the invention, one or more of the sequences represented by OspA Classes I-IV are present in an antigenic polypeptide which also includes antigenic sequences of OspC as described above.

In addition, other peptide sequences may be included in the peptides and polypeptides of the invention. Such sequences include but are not limited to antigenic peptide sequences such as linker sequences which in and of themselves are antigenic.

Those of skill in the art will recognize that, while in some embodiments of the invention, the amino acid sequences that are chosen for inclusion in the peptides and polypeptides of the invention correspond exactly to the primary amino acid sequence of the original or native sequences of an OspA (or OspC) protein, this need not always be the case. The amino acid sequence of an epitope that is included in the peptides and polypeptides of the invention may be altered somewhat and still be suitable for use in the present invention. For example, certain conservative amino acid substitutions may be made without having a deleterious effect on the ability of the peptides and polypeptides to elicit an immune response. Those of skill in the art will recognize the nature of such conservative substitutions, for example, substitution of a positively charged amino acid for another positively charged amino acid (e.g. K for R or vice versa); substitution of a negatively charged amino acid for another negatively charged amino acid (e.g. D for E or vice versa); substitution of a hydrophobic amino acid for another hydrophobic amino acid (e.g. substitution of A, V, L, I, W, etc. for one another); etc. All such substitutions or alterations of the sequences of the peptides and polypeptides that are disclosed herein are intended to be encompassed by the present invention, so long as the resulting peptides and polypeptides still function to elicit a suitable immune response. In addition, the amino acid sequences that are included in the chimeric proteins of the invention need not encompass a full length native peptide or polypeptide. Those of skill in the art will recognize that truncated versions of amino acid sequences that are known to be or to contain antigenic peptides and/or polypeptides may, for a variety of reasons, be preferable for use in the practice of the invention, so long as the criteria set forth for an epitope is fulfilled by the sequence. Amino acid sequences that are so substituted or otherwise altered may be referred to herein as "based on" or "derived from" the original wild type or native sequence. In general, the OspA or OspC proteins from which the linear epitopes are "derived" or on which the linear epitopes are "based" are the OspA or OspC proteins as they occur in nature. These natural OspA/OspC proteins may alternatively be referred to as native or wildtype proteins.

Such changes to the primary sequence may be introduced for any of a variety of reasons, for example, to eliminate or introduce a protease cleavage site, to increase or decrease solubility, to promote or discourage intra- or inter-molecular interactions such as folding, ionic interactions, salt bridges, etc, which might otherwise interfere with the presentation and accessibility of the individual epitopes along the length of a peptide or polypeptide. All such changes are intended to be encompassed by the present invention, so long as the resulting amino acid sequence functions to elicit a protective antibody response in a host to whom it is administered. In general, such substituted sequences will be at least about 50% identical to the corresponding sequence in the native protein, preferably about 60 to 70, or even 70 to 80, or 80 to 90% identical to the wild type sequence, and preferably about 95, 96, 97, 98, 99, or even 100% identical to a native OspA (or OspC) sequence. The reference native OspA or OspC sequence may be from any suitable type of *Borrelia*, e.g. from any *Borrelia* which is known to infect mammals.

In some embodiments of the invention, the individual linear epitopes in the chimeric vaccinogen are separated from one another by intervening sequences that are more or less neutral in character, i.e. they do not in and of themselves elicit an immune response to *Borrelia*. Such sequences may or may not be present between the epitopes of a chimera. If present, they may, for example, serve to separate the epitopes and contribute to the steric isolation of the epitopes from each other. Alternatively, such sequences may be simply artifacts of recombinant processing procedures, e.g. cloning procedures. Such sequences are typically known as linker or spacer peptides, many examples of which are known to those of skill in the art. See, for example, Crasto, C. J. and J. A. Feng. 2000. LINKER: a program to generate linker sequences for fusion proteins. Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers. In addition, other elements may be present in the chimeric proteins, for example leader sequences or sequences that "tag" the protein to facilitate purification or detection of the protein, examples of which include but are not limited to histidine tags, detection tags (e.g. S-tag, or Flag-tag), other antigenic amino acid sequences such as known T-cell epitope containing sequences and protein stabilizing motifs, etc. In addition, the chimeric proteins may be chemically modified, e.g. by amidation, sulfonylation, lipidation, or other techniques that are known to those of skill in the art.

The invention further provides nucleic acid sequences that encode the chimeric proteins of the invention. Such nucleic acids include DNA, RNA, and hybrids thereof, and the like. Further, the invention comprehends vectors which contain or house such coding sequences. Examples of suitable vectors include but are not limited to plasmids, cosmids, viral based vectors, expression vectors, etc. In a preferred embodiment, the vector will be a plasmid expression vector.

The chimeric polypeptides of the invention may be produced by any suitable method, many of which are known to those of skill in the art. For example, they may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.). In some embodiments, the polypeptides are produced using chemical synthesis methods.

The present invention also provides compositions for use in eliciting an immune response. The compositions may be utilized as vaccines to prevent or treat *Borrelia* infection, particularly when manifested as Lyme disease (Lyme borreliosis). By eliciting an immune response, we mean that administration of the antigen causes the synthesis of specific antibodies (at a titer as described above) and/or cellular proliferation, as measured, e.g. by $^3$H thymidine incorporation, or by other known techniques. By "vaccine" we mean a chimeric or fusion polypeptide that elicits an immune response which results in protection of an organicism against challenge with *Borrelia*. The protective response either wholly or partially prevents or arrests the development of symptoms related to *Borrelia* infection (i.e. the symptoms of Lyme disease), in comparison to a non-vaccinated (e.g. adjunct alone) control organisms, in which disease progression is not prevented. The compositions include one or more isolated and substantially purified chimeric peptides or polypeptides as described herein, and a pharmacologically suitable carrier. The chimeric polypeptides or proteins in the composition may be the same or different, i.e. the composition may be a "cocktail" of different chimeras, or a composition containing only a single type of chimera. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of chimeric protein in the formulations may vary. However, in general, the amount in the formulations will be from about 0.01-99%, weight/volume.

The methods involve administering a composition comprising a chimeric recombinant protein in a pharmacologically acceptable carrier to a mammal. The mammal may be a human, but this need not always be the case, as veterinary applications of this technology are also contemplated. The vaccine preparations of the present invention may be administered by any of the many suitable means which are well known to those of skill in the art, including but not limited to by injection, inhalation, orally, intranasally, by ingestion of a food product containing the chimeric protein, etc. In preferred embodiments, the mode of administration is subcutaneous or intramuscular. In addition, the compositions may be administered in conjunction with other treatment modalities such as substances that boost the immune system, various anti-bacterial chemotherapeutic agents, antibiotics, and the like.

The present invention provides methods to elicit an immune response to *Borrelia* and to vaccinate against *Borrelia* infection in mammals. In one embodiment, the mammal is a human. However, those of skill in the art will recognize that other mammals exist for which such vaccinations would also be desirable, e.g. the preparations may also be used for veterinary purposes. Examples include but are not limited to companion "pets" such as dogs, cats, etc.; food source, work and recreational animals such as cattle, horses, oxen, sheep, pigs, goats, and the like; or even wild animals that serve as a reservoir of *Borrelia* (e.g. mice, deer, etc).

The invention also provides a diagnostic and a method for using the diagnostic to identify individuals who have antibodies to the epitopes contained within the chimeric polypeptides of the invention. A biological sample from an individual (e.g. a human, a deer, or other mammals susceptible to infection by *Borrelia* spirochetes) suspected of having been exposed to *Borrelia*, or at risk for being exposed to *Borrelia*, is contacted with the chimeric proteins of the invention. Using known methodology, the presence or absence of a binding reaction between the chimeric protein and antibodies in the biological sample is detected. A positive result (i.e. binding occurs, thus antibodies are present) indicates that the individual has been exposed to and/or is infected with *Borrelia*. Further, the diagnostic aspects of the invention are not confined to clinical use or home use, but may also be valuable for use in the laboratory as a research tool, e.g. to identify *Borrelia* spirochetes isolated from ticks, to investigate the geographical distribution of *Borrelia* species and strains, etc.

The present invention also encompasses antibodies to the epitopes and/or to the chimeric polypeptides disclosed herein. Such antibodies may be polyclonal, monoclonal or chimeric, and may be generated in any manner known to those of skill in the art. In a preferred embodiment of the invention, the antibodies are bactericidal (borreliacidal), i.e. exposure of *Borrelia* spirochetes to the antibodies causes death of the spirochetes. Such antibodies may be used in a variety of ways, e.g. as detection reagents to diagnose prior exposure to *Borrelia*, as a reagent in a kit for the investigation of *Borrelia*, to treat *Borrelia* infections, etc.

Alternatively, appropriate antigen fragments or antigenic sequences or epitopes may be identified by their ability, when included in a chimeric protein, to elicit suitable antibody production to the epitope in a host to which the chimeric protein is administered. Those of skill in the art will recognize that definitions of antibody titer may vary. Herein, "titer" is taken to be the inverse dilution of antiserum that will bind one half of the available binding sites on an ELISA well coated with 100 ng of test protein. In general, suitable antibody production is characterized by an antibody titer in the range of from about 100 to about 100,000, and preferably in the range of from about 10,000 to about 10,000,000. Alternatively, and particularly in diagnostic assays, the "titer" should be about three times the background level of binding. For example, to be considered "positive", reactivity in a test should be at least three times greater than reactivity detected in serum from uninfected individuals. Preferably, the antibody response is protective, i.e. prevents or lessens the development of symptoms of disease in a vaccinated host that is later exposed to *Borrelia*, compared to an unvaccinated host.

The following Examples are provided to illustrate various embodiments of the invention, but should not be considered as limiting in any way.

EXAMPLES

Example 1. Identification of Linear Immunodominant Epitopes of *Borrelia* OspA Protein Materials and Methods
Recombinant Protein Production Fragments of the outer surface protein A (OspA) gene were amplified by PCR using high fidelity DNA polymerase (Phusion HF, New England Biolabs), and the amplicons purified by agarose gel electrophoresis and gel extraction. Overhangs were generated by treatment with T4 polymerase to allow ligase-independent annealing to the pET-32 Ek/LIC vector. The annealed vector was transformed into *Escherichia coli*, and the transformants were selected for ampicillin resistance, and were screened for the presence of the OspA gene fragment by PCR. Plasmids were then extracted from the transformants and the sequence confirmed by DNA sequencing (MWG Biotech). The plasmids were then used to transform *E. coli* BL21 (DE3) cells for protein production.

To generate recombinant proteins, BL21(DE3) cells were grown at 37° C. to an $OD_{600}$ of 0.5, then 1 mM IPTG was added to induce protein expression, and the cells were maintained at 37° C. for an additional 3 hours. The pET-32 Ek/LIC vector encodes a 17.1 kDa N-terminal protein tagging sequence which includes a hexahistidine motif that was used to purify the r-proteins by Ni-NTA nickel affinity chromatography, according to the manufacturer's protocol (Qiagen). The purified proteins were quantified by the bicinchoninic acid assay (Pierce).
Generation of Murine Infection Serum

*Borrelia burgdorferi* strains B31M1, LDP74, and B331 were grown to late log phase in BSK-H medium (Sigma). The cells were washed with fresh medium, quantified by microscopy, and diluted in BSK-H medium to $10^4$ cells per 0.1 mL of medium. Strain C3H/HeJ mice were infected with $10^4$ cells by subcutaneous injection between the scapulae, with 5 mice infected with each spirochete strain. The mice were bled at week 6 by tail nick, and infection was confirmed by culture of a 2 mm ear punch biopsy. Serum was prepared from the infected mouse blood samples, and will be referred to hereafter as infection serum.

Mapping of Linear B-Cell Epitopes on OspA

Figure 3:
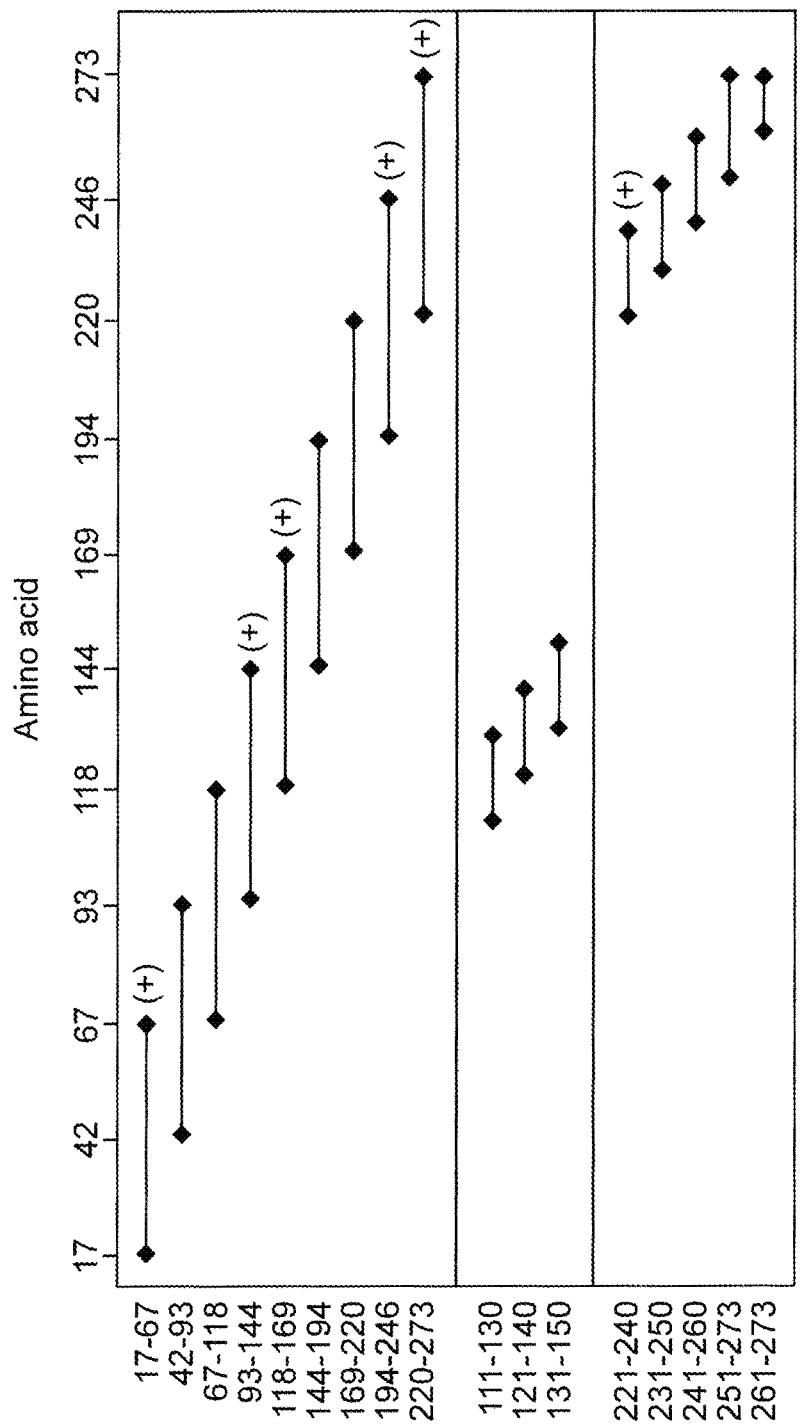
FIG. 3. Schematic of subfragments used to map linear epitopes in OspA. The initial screening of ~50 amino acid subfragments was followed by targeted screening of overlapping ~20 amino acid fragments to more accurately define the epitope location. Fragments detected by one or more mouse sera are denoted by a (+).

To map linear B-cell epitopes, overlapping recombinant subfragments of OspA were separated by 15% SDS-PAGE and blotted to PVDF. The membranes were blocked with 5% NFDM in PBS-T, and probed with mouse infection sera (1:500 dilution). To assess equality of protein loading, one blot was probed with a mouse monoclonal antibody specific to the hexahistidine motif in the expression tag sequence. The blots were then washed and probed with peroxidase-conjugated goat-anti-mouse IgG antiserum (1:20000; Pierce). The blots were washed, incubated with a chemiluminescent substrate (Supersignal West Pico; Pierce), and exposed to film. When reactive OspA fragments were determined, a series of smaller overlapping subfragments was made to further resolve the location of the linear epitope (FIG. 3).

OspA Sequence Analysis

The full length ospA gene from the *Borrelia* strains used to produce infection sera were PCR amplified and cloned into the pET-46 Ek/LIC vector as described above, and the DNA sequences were aligned and compared. In addition, the 204 full length OspA sequences from the Lyme spirochetes *B. burgdorferi*, *B. garinii*, and *B. afzelii* that are available in the NCBI databases were aligned and analyzed for polymorphisms in the epitope containing regions. This was done by multisequence alignment using ClustalX, and generation of neighbor joining phylogenetic trees. These analyses were done on the full length OspA gene, as well as on the epitope-containing subfragments. Once the alignments and trees were complete, representative sequences were extracted that demonstrate extant sequence variants, which may correspond to antigenic variants. Analytical tools included ClustalX, Bioedit, and TreeView.

Results:

Location of OspA Linear Epitopes

Figure 4:
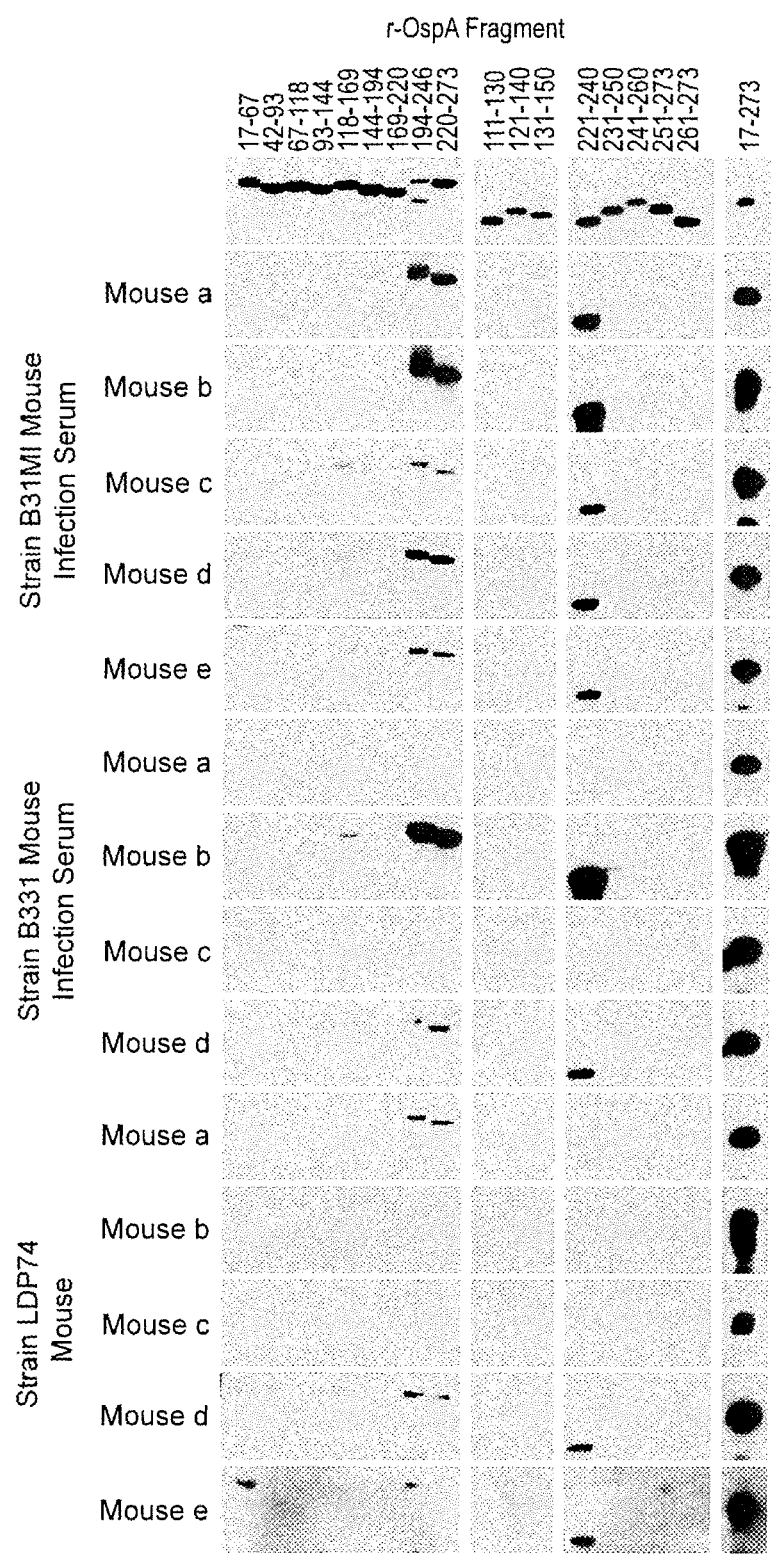
FIG. 4. Alignment of OspA sequences from the three *B. burgdorferi* strains used to infect mice for OspA epitope mapping.

A western blot-based search for linear B-cell epitopes on OspA revealed several amino acid sequences that were reactive with antibodies generated during murine infection (FIG. 4). The reactive subfragments are located at the N-terminus (amino acids 17-67; noted in a single mouse), within a central single layer beta-sheet (amino acids 94-144, and 119-169; seen in multiple mice), and within a membrane-distal loop (amino acids 194-246 and 220-273; highly reactive in multiple mice). High resolution mapping of the beta-sheet epitope containing region failed to further localize the epitope. The most reactive linear epitope was found in the membrane distal loop, and subsequent high resolution mapping localized it to amino acids 221-240. The pattern of reactivity varied somewhat in intensity between mice, but was observed in sera from mice infected with each of the three test *Borrelia* strains.

OspA Sequence Analysis

Comparison of sequences among the three *Borrelia* strains used to infect mice revealed either one or two amino acid differences among them, at amino acid positions 39 (K/N) and 149 (G/E) (FIG. 5). An analysis of available OspA sequences demonstrated several major clades, which split primarily along species lines (*B. burgdorferi*, *B. garinii*, and *B. afzelii*). To better understand the impact of the clades on the development of an epitope-based vaccine, the 221-240 region was analyzed separately, aligned, and a neighbor joining tree created. This also demonstrated the presence of distinct clades of this epitope containing region, again separated primarily by species. There were 2 predominant epitope region sequences within *B. burgdorferi*, 5 within *B. garinii*, and 1 within *B. afzelii* derived OspA sequences. The 221-240 amino acid regions in each of these predominant groups is shown in Table 1. Representative alignments of the other three epitope-containing sequences are shown in Table 2. Using the methods described above, the potential variants of these epitopes can be easily analyzed.

Discussion:

The mapping of novel linear B-cell epitopes in OspA represents a significant advance in the development of second-generation Lyme disease vaccines. Previous research has primarily focused on known conformational epitopes, primarily the epitope recognized by the LA-2 monoclonal antibody. Linear OspA epitopes have been described, however, this study is novel in its use of serum derived from mice infected with clonal *Borrelia* populations. The similar epitope recognition pattern during infection with three distinct *Borrelia burgdorferi* strains further supports the relevance of these epitope containing regions during infection. While OspA is expressed during in vitro culture, it is normally downregulated upon exposure to the mammalian environment or during the tick blood meal during the normal enzootic cycle. Because of this regulation, it is likely that the OspA protein was expressed only for a short time during the infection, which may account for the variability in the intensity of responsiveness between mice. This apparent variability may be enhanced by the IgG-specific screening technique, requiring the B-cells of the infected mice to progress to a more mature immune response and undergo immunoglobulin heavy chain class switching.

Figure 6:
FIG. 6. Structural representation of OspA highlighting a linear epitope-containing region. A ribbon diagram of OspA crystal structure (1FJ1) highlights amino acids 221-240 (gray) that contain a mapped linear epitope. The box surrounds the three loop regions that define the previously described protective LA-2 conformational epitope. The protein N-terminus is at the bottom of the diagram.

The large degree of intraspecies conservation at the mapped epitope-containing regions is of particular advantage in development of a peptide or chimeric vaccine. For example, since *B. burgdorferi* is the only species associated with Lyme disease in North America, the occurrence of only a limited number of phylogenetic clades of OspA is particularly advantageous. At the epitope level, the number of major clades is also limited, with only two major antigenically distinct clades representing the large majority of the 221-240 epitope containing region. *Borrelia afzelii*, which occurs only in Europe and Asia, is limited to a single clade at this region, and *B. garinii* has approximately 6 clades, several of which are closely related, though it is not yet known if they are antigenically cross-reactive. It is clear that in order for broad protection to be achieved by a peptide vaccine approach, the use of a single OspA epitope sequence is not possible. For that reason, the development of a multi-epitope chimeric vaccine based on OspA epitope variants or on a combination of epitope variants of OspA and OspC is highly desirable. In addition, a significant advantage to the use of defined epitope containing sequences is the ability to avoid segments of the OspA molecule that have been reported to be associated with development of autoimmune responses. While there is disagreement in the literature as to the incidence of these responses caused by anti-OspA antibodies or anti-OspA immune responses, it is advantageous to avoid those portions of OspA that have been implicated (FIG. 6).

Example 2

When administered to test mammals, this chimeric polypeptide construct comprising at least one 221-240 epitope containing region, and usually two or more 221-240 epitope containing regions from of different phyletic types, is found to elicit a robust immune response, and to provide protection from the development of Lyme disease.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A recombinant or synthetic fusion protein comprising two or more linear epitopes from *Borrelia* outer surface protein A (OspA), wherein at least two of the two or more linear epitopes are from different *Borrelia* species, and wherein
   i) one of the two or more linear epitopes is STLTITVNSKKTKDLVFTKE (SEQ ID NO: 1), or a sequence that is at least 95% identical to SEQ ID NO: 1, and SEQ ID NO: 1 is from *B. burgdorferi;* and
   ii) another of the two or more linear epitopes is KTLTVSADSKKIKDFVFLTD (SEQ ID NO: 15) or a sequence that is at least 95% identical to SEQ ID NO: 15, and SEQ ID NO: 15 is from *B. garinii.*

2. The recombinant or synthetic fusion protein of claim 1, wherein the two or more linear epitopes from *Borrelia* outer surface protein A (Osp A) include
   i) STLTITVNSKKTKDLVFTKE (SEQ ID NO: 1); and
   ii) KTLTVSADSKKIKDFVFLTD (SEQ ID NO: 15).

* * * * *

```
                         SEQUENCE LISTING

<160> NUMBER OF SEQ ID NOS: 76

<210> SEQ ID NO 1
<211> LENGTH: 20
<212> TYPE: PRT
<213> ORGANISM: Borrelia burgdorferi

<400> SEQUENCE: 1

Ser Thr Leu Thr Ile Thr Val Asn Ser Lys Lys Thr Lys Asp Leu Val
1               5                   10                  15

Phe Thr Lys Glu
            20

<210> SEQ ID NO 2
<211> LENGTH: 20
<212> TYPE: PRT
<213> ORGANISM: Borrelia burgdorferi

<400> SEQUENCE: 2

Ser Thr Leu Thr Ile Ile Val Asp Ser Lys Asn Lys Thr Lys Leu Val
1               5                   10                  15

Phe Thr Lys Gln
            20

<210> SEQ ID NO 3
<211> LENGTH: 20
<212> TYPE: PRT
<213> ORGANISM: Borrelia burgdorferi

<400> SEQUENCE: 3

Ser Thr Leu Thr Ile Ser Lys Asn Arg Thr Lys Thr Lys Gln Leu Val
1               5                   10                  15

Phe Thr Lys Glu
            20

<210> SEQ ID NO 4
<211> LENGTH: 20
<212> TYPE: PRT
<213> ORGANISM: Borrelia burgdorferi

<400> SEQUENCE: 4

Ser Thr Leu Thr Ile Ser Ala Asn Ser Lys Lys Thr Lys Asp Leu Val
1               5                   10                  15

Phe Leu Thr Asn
            20

<210> SEQ ID NO 5
<211> LENGTH: 20
<212> TYPE: PRT
<213> ORGANISM: Borrelia burgdorferi

<400> SEQUENCE: 5

Ser Thr Leu Thr Ile Thr Val Asn Asn Lys Lys Thr Lys Ala Leu Val
1               5                   10                  15

Phe Thr Lys Gln
            20
```

<210> SEQ ID NO 6
<211> LENGTH: 20
<212> TYPE: PRT
<213> ORGANISM: Borrelia burgdorferi

<400> SEQUENCE: 6

Ser Thr Leu Thr Ile Ser Val Asn Ser Lys Lys Thr Thr Gln Leu Val
1               5                   10                  15

Phe Thr Lys Gln
            20

<210> SEQ ID NO 7
<211> LENGTH: 20
<212> TYPE: PRT
<213> ORGANISM: Borrelia burgdorferi

<400> SEQUENCE: 7

Ser Thr Leu Thr Ile Ser Val Asn Ser Lys Lys Thr Lys Asn Ile Val
1               5                   10                  15

Phe Thr Lys Glu
            20

<210> SEQ ID NO 8
<211> LENGTH: 20
<212> TYPE: PRT
<213> ORGANISM: Borrelia burgdorferi

<400> SEQUENCE: 8

Ser Thr Leu Thr Ile Ser Val Asn Ser Gln Lys Thr Lys Asn Leu Val
1               5                   10                  15

Phe Thr Lys Glu
            20

<210> SEQ ID NO 9
<211> LENGTH: 20
<212> TYPE: PRT
<213> ORGANISM: Borrelia garinii

<400> SEQUENCE: 9

Asn Thr Leu Thr Val Ser Ala Asp Ser Lys Lys Ile Lys Asp Phe Val
1               5                   10                  15

Phe Leu Thr Asp
            20

<210> SEQ ID NO 10
<211> LENGTH: 20
<212> TYPE: PRT
<213> ORGANISM: Borrelia garinii

<400> SEQUENCE: 10

Ser Thr Leu Thr Ile Ser Lys Asn Ser Gln Lys Thr Lys Gln Leu Val
1               5                   10                  15

Phe Thr Lys Glu
            20

<210> SEQ ID NO 11
<211> LENGTH: 20
<212> TYPE: PRT
<213> ORGANISM: Borrelia garinii

<400> SEQUENCE: 11

Ser Thr Leu Thr Ile Ser Ala Lys Asn Lys Thr Lys Asp Leu Val
1               5                   10                  15

Phe Thr Lys Gln
            20

<210> SEQ ID NO 12
<211> LENGTH: 20
<212> TYPE: PRT
<213> ORGANISM: Borrelia garinii

<400> SEQUENCE: 12

Ser Thr Leu Lys Ile Ser Lys Asn Ser Lys Thr Lys Gln Leu Val
1               5                   10                  15

Phe Thr Lys Glu
            20

<210> SEQ ID NO 13
<211> LENGTH: 20
<212> TYPE: PRT
<213> ORGANISM: Borrelia garinii

<400> SEQUENCE: 13

Ser Thr Leu Thr Ile Ser Ala Lys Ser Lys Thr Lys Asp Leu Val
1               5                   10                  15

Phe Thr Lys Gln
            20

<210> SEQ ID NO 14
<211> LENGTH: 20
<212> TYPE: PRT
<213> ORGANISM: Borrelia garinii

<400> SEQUENCE: 14

Ser Thr Leu Thr Ile Ser Ala Asn Asn Lys Lys Thr Lys Asp Leu Val
1               5                   10                  15

Phe Thr Lys Gln
            20

<210> SEQ ID NO 15
<211> LENGTH: 20
<212> TYPE: PRT
<213> ORGANISM: Borrelia garinii

<400> SEQUENCE: 15

Lys Thr Leu Thr Val Ser Ala Asp Ser Lys Lys Ile Lys Asp Phe Val
1               5                   10                  15

Phe Leu Thr Asp
            20

<210> SEQ ID NO 16
<211> LENGTH: 20
<212> TYPE: PRT
<213> ORGANISM: Borrelia garinii

<400> SEQUENCE: 16

Ser Thr Leu Thr Ile Ser Ala Lys Asn Lys Lys Thr Thr Asp Leu Val
1               5                   10                  15

Phe Thr Lys Gln
            20

<210> SEQ ID NO 17
<211> LENGTH: 20

<212> TYPE: PRT
<213> ORGANISM: Borrelia garinii

<400> SEQUENCE: 17

Ser Thr Leu Thr Ile Ser Lys Asn Ser Arg Lys Thr Lys Gln Leu Val
1               5                   10                  15

Phe Thr Lys Glu
            20

<210> SEQ ID NO 18
<211> LENGTH: 20
<212> TYPE: PRT
<213> ORGANISM: Borrelia garinii

<400> SEQUENCE: 18

Ser Thr Leu Thr Ile Ser Val Asn Ser Arg Lys Thr Lys Asn Leu Val
1               5                   10                  15

Phe Thr Lys Glu
            20

<210> SEQ ID NO 19
<211> LENGTH: 51
<212> TYPE: PRT
<213> ORGANISM: Borrelia burgdorferi

<400> SEQUENCE: 19

Cys Lys Gln Asn Val Ser Ser Leu Asp Glu Lys Asn Ser Val Ser Val
1               5                   10                  15

Asp Leu Pro Gly Glu Met Lys Val Leu Val Ser Lys Glu Lys Asn Lys
            20                  25                  30

Asp Gly Lys Tyr Asp Leu Ile Ala Thr Val Asp Lys Leu Glu Leu Lys
        35                  40                  45

Gly Thr Ser
    50

<210> SEQ ID NO 20
<211> LENGTH: 51
<212> TYPE: PRT
<213> ORGANISM: Borrelia garinii

<400> SEQUENCE: 20

Cys Lys Gln Asn Val Ser Ser Leu Asp Glu Lys Asn Ser Val Ser Val
1               5                   10                  15

Asp Leu Pro Gly Gly Met Thr Val Leu Val Ser Lys Glu Lys Asp Lys
            20                  25                  30

Asp Gly Lys Tyr Ser Leu Glu Ala Thr Val Asp Lys Leu Glu Leu Lys
        35                  40                  45

Gly Thr Ser
    50

<210> SEQ ID NO 21
<211> LENGTH: 51
<212> TYPE: PRT
<213> ORGANISM: Borrelia afzelii

<400> SEQUENCE: 21

Cys Lys Gln Asn Val Ser Ser Leu Asp Glu Lys Asn Ser Ala Ser Val
1               5                   10                  15

Asp Leu Pro Gly Glu Met Lys Val Leu Val Ser Lys Glu Lys Asp Lys
            20                  25                  30

Asp Gly Lys Tyr Ser Leu Lys Ala Thr Val Asp Lys Ile Glu Leu Lys
            35                  40                  45

Gly Thr Ser
    50

<210> SEQ ID NO 22
<211> LENGTH: 51
<212> TYPE: PRT
<213> ORGANISM: Borrelia burgdorferi

<400> SEQUENCE: 22

Leu Gly Gln Thr Thr Leu Glu Val Phe Lys Glu Asp Gly Lys Thr Leu
1               5                   10                  15

Val Ser Lys Lys Val Thr Ser Lys Asp Lys Ser Ser Thr Glu Glu Lys
            20                  25                  30

Phe Asn Glu Lys Gly Glu Val Ser Glu Lys Ile Ile Thr Arg Ala Asp
            35                  40                  45

Gly Thr Arg
    50

<210> SEQ ID NO 23
<211> LENGTH: 51
<212> TYPE: PRT
<213> ORGANISM: Borrelia garinii

<400> SEQUENCE: 23

Leu Ser Gln Thr Lys Phe Glu Ile Phe Lys Glu Asp Gly Lys Thr Leu
1               5                   10                  15

Val Ser Lys Lys Val Thr Leu Lys Asp Lys Ser Ser Thr Glu Glu Lys
            20                  25                  30

Phe Asn Glu Lys Gly Glu Thr Ser Glu Lys Thr Ile Val Arg Ala Asn
            35                  40                  45

Gly Thr Arg
    50

<210> SEQ ID NO 24
<211> LENGTH: 51
<212> TYPE: PRT
<213> ORGANISM: Borrelia afzelii

<400> SEQUENCE: 24

Leu Ser Lys Pro Thr Phe Glu Leu Phe Lys Gly Asp Gly Glu Thr Leu
1               5                   10                  15

Val Ser Arg Lys Val Ser Ser Lys Asp Lys Thr Ser Thr Asp Glu Met
            20                  25                  30

Phe Asn Glu Lys Gly Glu Leu Ser Ala Lys Thr Met Thr Arg Glu Asn
            35                  40                  45

Gly Thr Lys
    50

<210> SEQ ID NO 25
<211> LENGTH: 51
<212> TYPE: PRT
<213> ORGANISM: Borrelia burgdorferi

<400> SEQUENCE: 25

Lys Ser Ser Thr Glu Glu Lys Phe Asn Glu Lys Gly Glu Val Ser Glu
1               5                   10                  15

Lys Ile Ile Thr Arg Ala Asp Gly Thr Arg Leu Glu Tyr Thr Gly Ile
            20                  25                  30

```
Lys Ser Asp Gly Ser Gly Lys Ala Lys Glu Val Leu Lys Gly Tyr Val
            35                  40                  45

Leu Glu Gly
    50

<210> SEQ ID NO 26
<211> LENGTH: 51
<212> TYPE: PRT
<213> ORGANISM: Borrelia garinii

<400> SEQUENCE: 26

Lys Ser Ser Thr Glu Glu Lys Phe Asn Glu Lys Gly Glu Thr Ser Glu
1               5                   10                  15

Lys Thr Ile Val Arg Ala Asn Gly Thr Arg Leu Glu Tyr Thr Asp Ile
            20                  25                  30

Lys Ser Asp Gly Ser Gly Lys Ala Lys Glu Val Leu Lys Asp Phe Thr
            35                  40                  45

Leu Glu Gly
    50

<210> SEQ ID NO 27
<211> LENGTH: 51
<212> TYPE: PRT
<213> ORGANISM: Borrelia afzelii

<400> SEQUENCE: 27

Lys Thr Ser Thr Asp Glu Met Phe Asn Glu Lys Gly Glu Leu Ser Ala
1               5                   10                  15

Lys Thr Met Thr Arg Glu Asn Gly Thr Lys Leu Glu Tyr Thr Glu Met
            20                  25                  30

Lys Ser Asp Gly Thr Gly Lys Ala Lys Glu Val Leu Lys Asn Phe Thr
            35                  40                  45

Leu Glu Gly
    50

<210> SEQ ID NO 28
<211> LENGTH: 72
<212> TYPE: PRT
<213> ORGANISM: Borrelia garinii

<400> SEQUENCE: 28

Ser Glu Ala Phe Thr Asn Lys Leu Lys Glu Lys His Ala Glu Leu Gly
1               5                   10                  15

Val Asn Gly Gly Asp Thr Thr Asp Asn Ala Lys Ala Ala Ile Phe
            20                  25                  30

Lys Thr His Pro Thr Lys Asp Lys Gly Val Glu Asp Leu Glu Lys Leu
            35                  40                  45

Ser Glu Ser Val Lys Ser Leu Leu Lys Ala Ala Gln Ala Ala Leu Ser
    50                  55                  60

Asn Ser Val Lys Glu Leu Thr Ser
65                  70

<210> SEQ ID NO 29
<211> LENGTH: 72
<212> TYPE: PRT
<213> ORGANISM: Borrelia garinii

<400> SEQUENCE: 29

Ser Asp Lys Phe Thr Lys Lys Leu Thr Asp Ser His Ala Gln Leu Gly
```

-continued

```
                1               5                  10                 15
            Ala Val Gly Gly Ala Ile Asn Asp Asp Arg Ala Lys Glu Ala Ile Leu
                        20                  25                  30
            Lys Thr His Gly Thr Asn Asp Lys Gly Ala Lys Glu Leu Lys Glu Leu
                        35                  40                  45
            Ser Glu Ser Val Glu Ser Leu Ala Lys Ala Ala Gln Ala Ala Leu Ala
                    50                  55                  60
            Asn Ser Val Lys Glu Leu Thr Ser
            65                  70

<210> SEQ ID NO 30
<211> LENGTH: 70
<212> TYPE: PRT
<213> ORGANISM: Borrelia garinii

<400> SEQUENCE: 30

Ser Glu Ala Phe Thr Lys Lys Leu Lys Asp Asn Ala Gln Leu Gly
            1               5                  10                 15

Ile Gln Asn Val Gln Asp Val Glu Ala Lys Lys Ala Ile Leu Lys Thr
                        20                  25                  30

Asn Gly Asp Ile Ser Lys Gly Ala Lys Glu Leu Lys Glu Leu Phe Glu
                        35                  40                  45

Ser Val Glu Ser Leu Ala Lys Ala Ala Gln Ala Ala Leu Ala Asn Ser
                    50                  55                  60

Val Gln Glu Leu Thr Asn
            65                  70

<210> SEQ ID NO 31
<211> LENGTH: 70
<212> TYPE: PRT
<213> ORGANISM: Borrelia garinii

<400> SEQUENCE: 31

Ser Glu Ala Phe Thr Asn Arg Leu Lys Gly Ser His Ala Gln Leu Gly
            1               5                  10                 15

Val Ala Ala Ala Thr Asp Asp His Ala Lys Glu Ala Ile Leu Lys Ser
                        20                  25                  30

Asn Pro Thr Lys Asp Lys Gly Ala Lys Glu Leu Lys Asp Leu Ser Glu
                        35                  40                  45

Ser Val Glu Ser Leu Ala Lys Ala Ala Gln Glu Ala Leu Ala Asn Ser
                    50                  55                  60

Val Lys Glu Leu Thr Asn
            65                  70

<210> SEQ ID NO 32
<211> LENGTH: 70
<212> TYPE: PRT
<213> ORGANISM: Borrelia garinii

<400> SEQUENCE: 32

Ser Glu Ala Phe Thr Asn Arg Leu Thr Gly Ser His Ala Gln His Gly
            1               5                  10                 15

Val Ala Ala Ala Thr Asp Asp His Ala Lys Glu Ala Ile Leu Lys Ser
                        20                  25                  30

Asn Pro Thr Lys Asp Lys Gly Ala Lys Glu Leu Lys Asp Leu Ser Glu
                        35                  40                  45

Ser Val Glu Ser Leu Ala Lys Ala Ala Gln Glu Ala Leu Ala Asn Ser
                    50                  55                  60
```

Val Lys Glu Leu Thr Asn
65                  70

<210> SEQ ID NO 33
<211> LENGTH: 72
<212> TYPE: PRT
<213> ORGANISM: Borrelia garinii

<400> SEQUENCE: 33

Ser Glu Ala Phe Thr Asn Lys Leu Lys Glu Lys Thr Gln Glu Leu Ala
1               5                   10                  15

Val Ala Ala Gly Ala Ala Thr Asp Ile Asp Ala Lys Lys Ala Ile Leu
            20                  25                  30

Lys Thr Asn Arg Asp Lys Asp Leu Gly Ala Asp Glu Arg Gly Lys Leu
        35                  40                  45

Phe Lys Ser Val Glu Ser Leu Ser Lys Ala Ala Gln Glu Ala Ser Ala
    50                  55                  60

Asn Ser Val Lys Glu Leu Thr Ser
65                  70

<210> SEQ ID NO 34
<211> LENGTH: 72
<212> TYPE: PRT
<213> ORGANISM: Borrelia garinii

<400> SEQUENCE: 34

Ser Val Ala Phe Thr Ser Lys Leu Lys Ser Ser Asn Ala Gln Leu Gly
1               5                   10                  15

Val Ala Asn Gly Asn Ala Thr Asp Asp Asp Ala Lys Lys Ala Ile Leu
            20                  25                  30

Lys Thr Asn Thr Pro Asn Asp Lys Gly Ala Lys Glu Leu Lys Glu Leu
        35                  40                  45

Phe Glu Ser Val Glu Ser Leu Ala Lys Ala Ala Gln Ala Ala Leu Val
    50                  55                  60

Asn Ser Val Gln Glu Leu Thr Asn
65                  70

<210> SEQ ID NO 35
<211> LENGTH: 72
<212> TYPE: PRT
<213> ORGANISM: Borrelia garinii

<400> SEQUENCE: 35

Ser Glu Ala Phe Thr Lys Lys Leu Lys Asp Ser Asn Ala Gln Leu Gly
1               5                   10                  15

Met Gln Asn Gly Ala Ala Thr Asp Ala His Ala Lys Ala Ala Ile Leu
            20                  25                  30

Lys Thr Asp Ala Thr Lys Asp Lys Gly Ala Thr Glu Leu Gly Glu Leu
        35                  40                  45

Phe Lys Ser Val Glu Ser Leu Ser Lys Ala Ala Gln Glu Ala Ser Ala
    50                  55                  60

Asn Ser Val Lys Glu Leu Thr Ser
65                  70

<210> SEQ ID NO 36
<211> LENGTH: 70
<212> TYPE: PRT
<213> ORGANISM: Borrelia garinii

<400> SEQUENCE: 36

Ser Ala Ala Phe Thr Lys Lys Leu Gln Asp Gly His Val Asp Leu Gly
1               5                   10                  15

Lys Thr Asp Val Thr Asp Asp Asn Ala Lys Glu Ala Ile Leu Lys Thr
            20                  25                  30

Asn Pro Thr Lys Thr Lys Gly Ala Thr Glu Leu Glu Leu Phe Lys
            35                  40                  45

Ser Val Glu Gly Leu Val Lys Ala Ala Lys Ala Ser Ala Asn Ser
50                      55                  60

Val Lys Glu Leu Thr Ser
65                  70

<210> SEQ ID NO 37
<211> LENGTH: 70
<212> TYPE: PRT
<213> ORGANISM: Borrelia afzelii

<400> SEQUENCE: 37

Ser Glu Glu Phe Thr Asn Lys Leu Lys Ser Gly His Ala Asp Leu Gly
1               5                   10                  15

Lys Gln Asp Ala Thr Asp Asp His Ala Lys Ala Ala Ile Leu Lys Thr
            20                  25                  30

His Ala Thr Thr Asp Lys Gly Ala Lys Glu Phe Lys Asp Leu Phe Glu
            35                  40                  45

Ser Val Glu Gly Leu Leu Lys Ala Ala Gln Val Ala Leu Thr Asn Ser
50                      55                  60

Val Lys Glu Leu Thr Ser
65                  70

<210> SEQ ID NO 38
<211> LENGTH: 70
<212> TYPE: PRT
<213> ORGANISM: Borrelia afzelii

<400> SEQUENCE: 38

Ser Glu Glu Phe Thr Asn Lys Leu Lys Ser Gly His Ala Asp Leu Gly
1               5                   10                  15

Lys Gln Asp Ala Thr Asp Glu His Ala Lys Ala Ala Ile Leu Lys Thr
            20                  25                  30

His Ala Thr Thr Asp Lys Gly Ala Lys Glu Phe Lys Asp Leu Phe Glu
            35                  40                  45

Ser Val Glu Gly Leu Leu Lys Ser Ala Gln Val Ala Leu Thr Asn Ser
50                      55                  60

Val Lys Glu Leu Thr Asn
65                  70

<210> SEQ ID NO 39
<211> LENGTH: 70
<212> TYPE: PRT
<213> ORGANISM: Borrelia afzelii

<400> SEQUENCE: 39

Ser Glu Glu Phe Thr Asn Lys Leu Lys Gly Gly His Ala Glu Leu Gly
1               5                   10                  15

Leu Ala Ala Ala Thr Asp Glu Asn Ala Lys Lys Ala Ile Leu Lys Thr
            20                  25                  30

Asn Gly Thr Lys Asp Lys Gly Ala Glu Glu Leu Glu Lys Leu Phe Lys
            35                  40                  45

```
Ser Val Glu Ser Leu Ala Lys Ala Ala Lys Glu Ser Leu Thr Asn Ser
        50                  55                  60

Val Lys Glu Leu Thr Asn
65                  70

<210> SEQ ID NO 40
<211> LENGTH: 70
<212> TYPE: PRT
<213> ORGANISM: Borrelia afzelii

<400> SEQUENCE: 40

Ser Glu Ala Phe Thr Lys Lys Leu Gln Asp Ser Asn Ala Asp Leu Gly
1               5                   10                  15

Lys His Asn Ala Thr Asp Ala Asp Ser Lys Glu Ala Ile Leu Lys Thr
            20                  25                  30

Asn Gly Thr Lys Thr Lys Gly Ala Lys Glu Leu Glu Glu Leu Phe Lys
        35                  40                  45

Ser Val Glu Ser Leu Ser Lys Ala Ala Lys Glu Ala Leu Ser Asn Ser
        50                  55                  60

Val Lys Glu Leu Thr Ser
65                  70

<210> SEQ ID NO 41
<211> LENGTH: 70
<212> TYPE: PRT
<213> ORGANISM: Borrelia afzelii

<400> SEQUENCE: 41

Ser Glu Ala Phe Thr Lys Lys Leu Gln Asp Ser Asn Ala Asp Leu Gly
1               5                   10                  15

Lys His Asp Ala Thr Asp Ala Asp Ala Lys Lys Ala Ile Leu Lys Thr
            20                  25                  30

Asp Ala Thr Lys Asp Lys Gly Ala Lys Glu Leu Glu Glu Leu Phe Lys
        35                  40                  45

Ser Val Glu Ser Leu Ser Lys Ala Ala Lys Glu Ala Leu Ser Asn Ser
        50                  55                  60

Val Lys Glu Leu Thr Ser
65                  70

<210> SEQ ID NO 42
<211> LENGTH: 70
<212> TYPE: PRT
<213> ORGANISM: Borrelia afzelii

<400> SEQUENCE: 42

Ser Gln Asp Phe Ile Asn Lys Leu Lys Gly Gly His Ala Glu Leu Gly
1               5                   10                  15

Leu Val Ala Ala Thr Asp Ala Asn Ala Lys Ala Ala Ile Leu Lys Thr
            20                  25                  30

Asn Gly Asp Lys Thr Lys Gly Ala Asp Glu Phe Glu Lys Leu Phe Lys
        35                  40                  45

Ser Val Glu Gly Leu Leu Lys Ala Ala Gln Glu Ala Leu Thr Asn Ser
        50                  55                  60

Val Lys Glu Leu Thr Ser
65                  70

<210> SEQ ID NO 43
<211> LENGTH: 70
```

```
<212> TYPE: PRT
<213> ORGANISM: Borrelia afzelii

<400> SEQUENCE: 43

Ser Gln Asp Phe Ile Asn Lys Leu Lys Gly Gly His Ala Glu Leu Gly
1               5                   10                  15

Leu Ala Ala Ala Thr Asp Ala Asn Ala Lys Ala Ala Ile Leu Lys Thr
            20                  25                  30

Asn Gly Asp Lys Thr Lys Gly Ala Asp Glu Phe Glu Lys Leu Phe Lys
        35                  40                  45

Ser Val Glu Gly Leu Leu Lys Ala Ala Gln Glu Ala Leu Thr Asn Ser
    50                  55                  60

Val Lys Glu Leu Thr Thr
65                  70

<210> SEQ ID NO 44
<211> LENGTH: 70
<212> TYPE: PRT
<213> ORGANISM: Borrelia burgdorferi

<400> SEQUENCE: 44

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
            20                  25                  30

Asn Gly Thr Lys Thr Lys Gly Ala Glu Glu Leu Gly Lys Leu Phe Glu
        35                  40                  45

Ser Val Glu Val Leu Ser Lys Ala Ala Lys Glu Met Leu Ala Asn Ser
    50                  55                  60

Val Lys Glu Leu Thr Ser
65                  70

<210> SEQ ID NO 45
<211> LENGTH: 72
<212> TYPE: PRT
<213> ORGANISM: Borrelia burgdorferi

<400> SEQUENCE: 45

Ser Ala Ala Phe Thr Lys Lys Leu Ala Asp Ser Asn Ala Asp Leu Gly
1               5                   10                  15

Val Ala Ala Gly Asn Ala Thr Asp Asp Asn Ala Lys Arg Ala Ile Leu
            20                  25                  30

Lys Thr His Gly His Glu Asp Lys Gly Gly Lys Glu Leu Lys Glu Leu
        35                  40                  45

Ser Glu Ala Val Lys Ser Leu Leu Lys Ala Gln Ala Ala Leu Ala
    50                  55                  60

Asn Ser Val Gln Glu Leu Thr Ser
65                  70

<210> SEQ ID NO 46
<211> LENGTH: 70
<212> TYPE: PRT
<213> ORGANISM: Borrelia burgdorferi

<400> SEQUENCE: 46

Ser Glu Asp Phe Thr Asn Lys Leu Lys Asn Gly Asn Ala Gln Leu Gly
1               5                   10                  15

Leu Ala Ala Ala Thr Asp Asp Asn Ala Lys Ala Ala Ile Leu Lys Thr
            20                  25                  30
```

Asn Gly Thr Asn Asp Lys Gly Ala Lys Glu Leu Lys Asp Leu Ser Asp
            35                  40                  45

Ser Val Glu Ser Leu Val Lys Ala Ala Gln Val Met Leu Thr Asn Ser
    50                  55                  60

Val Lys Glu Leu Thr Ser
65                  70

<210> SEQ ID NO 47
<211> LENGTH: 70
<212> TYPE: PRT
<213> ORGANISM: Borrelia burgdorferi

<400> SEQUENCE: 47

Ser Thr Glu Phe Thr Asn Lys Leu Lys Ser Glu His Ala Val Leu Gly
1               5                   10                  15

Leu Asp Asn Leu Thr Asp Asp Asn Ala Gln Arg Ala Ile Leu Lys Lys
            20                  25                  30

His Ala Asn Lys Asp Lys Gly Ala Ala Glu Leu Glu Lys Leu Phe Lys
        35                  40                  45

Ala Val Glu Asn Leu Ser Lys Ala Ala Gln Asp Thr Leu Lys Asn Ala
    50                  55                  60

Val Lys Glu Leu Thr Ser
65                  70

<210> SEQ ID NO 48
<211> LENGTH: 72
<212> TYPE: PRT
<213> ORGANISM: Borrelia burgdorferi

<400> SEQUENCE: 48

Asn Lys Ala Phe Thr Asp Lys Leu Lys Ser Ser His Ala Glu Leu Gly
1               5                   10                  15

Ile Ala Asn Gly Ala Ala Thr Asp Ala Asn Ala Lys Ala Ala Ile Leu
            20                  25                  30

Lys Thr Asn Gly Thr Lys Asp Lys Gly Ala Gln Glu Leu Glu Lys Leu
        35                  40                  45

Phe Glu Ser Val Lys Asn Leu Ser Lys Ala Ala Gln Glu Thr Leu Asn
    50                  55                  60

Asn Ser Val Lys Glu Leu Thr Ser
65                  70

<210> SEQ ID NO 49
<211> LENGTH: 70
<212> TYPE: PRT
<213> ORGANISM: Borrelia burgdorferi

<400> SEQUENCE: 49

Ser Glu Ser Phe Thr Lys Lys Leu Ser Asp Asn Gln Ala Glu Leu Gly
1               5                   10                  15

Ile Glu Asn Ala Thr Asp Asp Asn Ala Lys Lys Ala Ile Leu Lys Thr
            20                  25                  30

His Asn Ala Lys Asp Lys Gly Ala Glu Glu Leu Val Lys Leu Ser Glu
        35                  40                  45

Ser Val Ala Gly Leu Leu Lys Ala Ala Gln Ala Ile Leu Ala Asn Ser
    50                  55                  60

Val Lys Glu Leu Thr Ser
65                  70

<210> SEQ ID NO 50
<211> LENGTH: 70
<212> TYPE: PRT
<213> ORGANISM: Borrelia burgdorferi

<400> SEQUENCE: 50

Ser Glu Lys Phe Thr Lys Lys Leu Ser Glu Ser His Ala Asp Ile Gly
1               5                   10                  15

Ile Gln Ala Ala Thr Asp Ala Asn Ala Lys Asp Ala Ile Leu Lys Thr
            20                  25                  30

Asn Pro Thr Lys Thr Lys Gly Ala Glu Glu Leu Asp Lys Leu Phe Lys
        35                  40                  45

Ala Val Glu Asn Leu Ser Lys Ala Ala Lys Glu Met Leu Ala Asn Ser
    50                  55                  60

Val Lys Asp Leu Gln Val
65                  70

<210> SEQ ID NO 51
<211> LENGTH: 70
<212> TYPE: PRT
<213> ORGANISM: Borrelia burgdorferi

<400> SEQUENCE: 51

Ser Glu Lys Phe Thr Lys Lys Leu Ser Glu Ser His Ala Asp Ile Gly
1               5                   10                  15

Ile Gln Ala Ala Thr Asp Ala Asn Ala Lys Asp Ala Ile Leu Lys Thr
            20                  25                  30

Asn Pro Thr Lys Thr Lys Gly Ala Glu Glu Leu Asp Lys Leu Phe Lys
        35                  40                  45

Ala Val Glu Asn Leu Ser Lys Ala Ala Lys Glu Met Leu Ala Asn Ser
    50                  55                  60

Val Lys Glu Leu Thr Ser
65                  70

<210> SEQ ID NO 52
<211> LENGTH: 70
<212> TYPE: PRT
<213> ORGANISM: Borrelia burgdorferi

<400> SEQUENCE: 52

Ser Glu Glu Phe Thr Ala Lys Leu Lys Gly Glu His Thr Asp Leu Gly
1               5                   10                  15

Lys Glu Gly Val Thr Asp Asp Asn Ala Lys Lys Ala Ile Leu Lys Thr
            20                  25                  30

Asn Asn Asp Lys Thr Lys Gly Ala Asp Glu Leu Glu Lys Leu Phe Glu
        35                  40                  45

Ser Val Lys Asn Leu Ser Lys Ala Ala Lys Glu Met Leu Thr Asn Ser
    50                  55                  60

Val Lys Glu Leu Thr Ser
65                  70

<210> SEQ ID NO 53
<211> LENGTH: 70
<212> TYPE: PRT
<213> ORGANISM: Borrelia burgdorferi

<400> SEQUENCE: 53

Ser Glu Lys Phe Thr Asp Lys Leu Lys Ser Glu Asn Ala Ala Leu Gly
1               5                   10                  15

```
Lys Gln Asp Ala Ser Asp Asp Ala Lys Lys Ala Ile Leu Lys Thr
            20                  25                  30

His Asn Asp Ile Thr Lys Gly Ala Lys Glu Leu Lys Glu Leu Ser Glu
            35                  40                  45

Ser Val Glu Thr Leu Leu Lys Ala Ala Lys Glu Met Leu Ala Asn Ser
        50                  55                  60

Val Lys Glu Leu Thr Ser
65                  70

<210> SEQ ID NO 54
<211> LENGTH: 70
<212> TYPE: PRT
<213> ORGANISM: Borrelia burgdorferi

<400> SEQUENCE: 54

Ser Glu Lys Phe Ala Gly Lys Leu Lys Asn Glu His Ala Ser Leu Gly
1               5                   10                  15

Lys Lys Asp Ala Thr Asp Asp Ala Lys Lys Ala Ile Leu Lys Thr
            20                  25                  30

His Gly Asn Thr Asp Lys Gly Ala Lys Glu Leu Lys Asp Leu Ser Asp
            35                  40                  45

Ser Val Glu Ser Leu Val Lys Ala Ala Lys Glu Met Leu Thr Asn Ser
        50                  55                  60

Val Lys Glu Leu Thr Ser
65                  70

<210> SEQ ID NO 55
<211> LENGTH: 70
<212> TYPE: PRT
<213> ORGANISM: Borrelia burgdorferi

<400> SEQUENCE: 55

Ser Glu Ala Phe Thr Asp Lys Leu Lys Asn Glu His Ala Ser Leu Gly
1               5                   10                  15

Lys Lys Asp Ala Thr Asp Asp Ala Lys Lys Ala Ile Leu Lys Thr
            20                  25                  30

Asn Val Asp Lys Thr Lys Gly Ala Asp Glu Leu Ile Lys Leu Ser Gly
            35                  40                  45

Ser Leu Glu Ser Leu Ser Lys Ala Ala Gln Ala Ile Leu Ala Asn Ser
        50                  55                  60

Val Lys Glu Leu Thr Ser
65                  70

<210> SEQ ID NO 56
<211> LENGTH: 70
<212> TYPE: PRT
<213> ORGANISM: Borrelia garinii

<400> SEQUENCE: 56

Ser Glu Lys Phe Thr Thr Lys Leu Arg Asp Ser His Ala Glu Leu Gly
1               5                   10                  15

Ile Gln Asn Val Gln Asp Asp Asn Ala Lys Arg Ala Ile Leu Lys Thr
            20                  25                  30

His Gly Asn Lys Asp Lys Gly Ala Lys Glu Leu Lys Glu Leu Ser Glu
            35                  40                  45

Ser Leu Glu Lys Leu Ser Lys Ala Ala Gln Ala Ala Leu Ala Asn Ser
        50                  55                  60
```

Val Gln Glu Leu Thr Ser
65              70

<210> SEQ ID NO 57
<211> LENGTH: 70
<212> TYPE: PRT
<213> ORGANISM: Borrelia garinii

<400> SEQUENCE: 57

Ser Glu Lys Phe Thr Thr Lys Leu Lys Asp Ser His Ala Glu Leu Gly
1               5                   10                  15

Ile Gln Ser Val Gln Asp Asp Asn Ala Lys Lys Ala Ile Leu Lys Thr
            20                  25                  30

His Gly Thr Lys Asp Lys Gly Ala Lys Glu Leu Glu Glu Leu Phe Lys
        35                  40                  45

Ser Leu Glu Ser Leu Ser Lys Ala Ala Gln Ala Ala Leu Thr Asn Ser
    50                  55                  60

Val Lys Glu Leu Thr Asn
65              70

<210> SEQ ID NO 58
<211> LENGTH: 71
<212> TYPE: PRT
<213> ORGANISM: Borrelia burgdorferi

<400> SEQUENCE: 58

Ser Glu Glu Phe Ser Thr Lys Leu Lys Asp Asn His Ala Gln Leu Gly
1               5                   10                  15

Ile Gln Gly Val Thr Asp Glu Asn Ala Lys Lys Ala Ile Leu Lys Ala
            20                  25                  30

Asn Ala Ala Gly Lys Asp Lys Gly Val Glu Glu Leu Glu Lys Leu Ser
        35                  40                  45

Gly Ser Leu Glu Ser Leu Ser Lys Ala Ala Lys Glu Met Leu Ala Asn
    50                  55                  60

Ser Val Lys Glu Leu Thr Ser
65              70

<210> SEQ ID NO 59
<211> LENGTH: 71
<212> TYPE: PRT
<213> ORGANISM: Borrelia burgdorferi

<400> SEQUENCE: 59

Ser Glu Glu Phe Ser Thr Lys Leu Lys Asp Asn His Ala Gln Leu Gly
1               5                   10                  15

Ile Gln Gly Val Thr Asp Glu Asn Ala Lys Lys Ala Ile Leu Lys Ala
            20                  25                  30

Asn Ala Ala Gly Lys Asp Lys Gly Val Glu Glu Leu Glu Lys Leu Ser
        35                  40                  45

Gly Ser Leu Glu Ser Leu Ser Lys Ala Ala Lys Glu Met Leu Ala Asn
    50                  55                  60

Ser Val Lys Ser Leu Gln Ser
65              70

<210> SEQ ID NO 60
<211> LENGTH: 70
<212> TYPE: PRT
<213> ORGANISM: Borrelia burgdorferi

<400> SEQUENCE: 60

```
Ser Glu Asp Phe Thr Lys Lys Leu Glu Gly Glu His Ala Gln Leu Gly
1               5                   10                  15

Ile Glu Asn Val Thr Asp Glu Asn Ala Lys Lys Ala Ile Leu Ile Thr
                20                  25                  30

Asp Ala Ala Lys Asp Lys Gly Ala Ala Glu Leu Glu Lys Leu Phe Lys
            35                  40                  45

Ala Val Glu Asn Leu Ala Lys Ala Ala Lys Glu Met Leu Ala Asn Ser
        50                  55                  60

Val Lys Glu Leu Thr Ser
65              70

<210> SEQ ID NO 61
<211> LENGTH: 72
<212> TYPE: PRT
<213> ORGANISM: Borrelia burgdorferi

<400> SEQUENCE: 61

Ser Asp Asp Phe Thr Lys Lys Leu Gln Ser Ser His Ala Gln Leu Gly
1               5                   10                  15

Val Ala Gly Gly Ala Thr Thr Asp Glu Glu Ala Lys Lys Ala Ile Leu
                20                  25                  30

Arg Thr Asn Ala Ile Lys Asp Lys Gly Ala Asp Glu Leu Glu Lys Leu
            35                  40                  45

Phe Lys Ser Val Glu Ser Leu Ala Lys Ala Ala Gln Asp Ala Leu Ala
        50                  55                  60

Asn Ser Val Asn Glu Leu Thr Ser
65                  70

<210> SEQ ID NO 62
<211> LENGTH: 80
<212> TYPE: PRT
<213> ORGANISM: Borrelia burgdorferi

<400> SEQUENCE: 62

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
                20                  25                  30

Asn Gly Thr Lys Thr Lys Gly Ala Glu Glu Leu Gly Lys Leu Phe Glu
            35                  40                  45

Ser Val Glu Val Leu Ser Lys Ala Ala Lys Glu Met Leu Ala Asn Ser
        50                  55                  60

Val Lys Glu Leu Thr Ser Pro Val Val Ala Glu Ser Pro Lys Lys Pro
65              70                  75                  80

<210> SEQ ID NO 63
<211> LENGTH: 80
<212> TYPE: PRT
<213> ORGANISM: Borrelia garinii

<400> SEQUENCE: 63

Ser Glu Thr Phe Thr Asn Lys Leu Lys Glu Lys His Thr Asp Leu Gly
1               5                   10                  15

Lys Glu Gly Val Thr Asp Ala Asp Ala Lys Glu Ala Ile Leu Lys Thr
                20

```
Ser Val Glu Val Leu Ser Lys Ala Ala Lys Glu Met Leu Ala Asn Ser
 50                  55                  60

Val Lys Glu Leu Thr Ser Pro Val Val Ala Glu Ser Pro Lys Lys Pro
 65                  70                  75                  80

<210> SEQ ID NO 64
<211> LENGTH: 80
<212> TYPE: PRT
<213> ORGANISM: Artificial
<220> FEATURE:
<223> OTHER INFORMATION: synthetic chimeric polypeptide

<400> SEQUENCE: 64

Ser Glu Thr Phe Thr Asn Lys Leu Lys Glu Lys His Thr Asp Leu Gly
  1               5                  10                  15

Lys Glu Gly Val Thr Asp Ala Asp Ala Lys Glu Ala Ile Leu Lys Thr
                 20                  25                  30

Asn Gly Thr Lys Thr Lys Gly Ala Glu Glu Leu Gly Lys Leu Phe Glu
             35                  40                  45

Ser Val Glu Val Leu Ser Lys Ala Ala Lys Glu Met Leu Ala Asn Ser
 50                  55                  60

Val Lys Glu Leu Thr Ser Pro Val Val Ala Glu Ser Pro Lys Lys Pro
 65                  70                  75                  80

<210> SEQ ID NO 65
<211> LENGTH: 569
<212> TYPE: PRT
<213> ORGANISM: Artificial
<220> FEATURE:
<223> OTHER INFORMATION: synthetic chimeric polypeptide

<400> SEQUENCE: 65

Ser Glu Thr Phe Thr Asn Lys Leu Lys Glu Lys His Thr Asp Leu Gly
  1               5                  10                  15

Lys Glu Gly Val Thr Asp Ala Asp Ala Lys Glu Ala Ile Leu Lys Thr
                 20                  25                  30

Asn Gly Thr Lys Thr Lys Gly Ala Glu Glu Leu Gly Lys Leu Phe Glu
             35                  40                  45

Ser Val Glu Val Leu Ser Lys Ala Ala Lys Glu Met Leu Ala Asn Ser
 50                  55                  60

Val Lys Glu Leu Thr Ser Ser Glu Glu Phe Ser Thr Lys Leu Lys Asp
 65                  70                  75                  80

Asn His Ala Gln Leu Gly Ile Gln Gly Val Thr Asp Glu Asn Ala Lys
                 85                  90                  95

Lys Ala Ile Leu Lys Ala Asn Ala Ala Gly Lys Asp Lys Gly Val Glu
                100                 105                 110

Glu Leu Glu Lys Leu Ser Gly Ser Leu Glu Ser Leu Ser Ser Glu Asp
                115                 120                 125

Phe Thr Lys Lys Leu Glu Gly Glu His Ala Gln Leu Gly Ile Glu Asn
            130                 135                 140

Val Thr Asp Glu Asn Ala Lys Lys Ala Ile Leu Ile Thr Asp Ala Ala
145                 150                 155                 160

Lys Asp Lys Gly Ala Ala Glu Leu Glu Lys Leu Phe Lys Ala Val Glu
                165                 170                 175

Asn Leu Ala Ala Lys Leu Lys Gly Glu His Thr Asp Leu Gly Lys Glu
            180                 185                 190

Gly Val Thr Asp Asp Asn Ala Lys Lys Ala Ile Leu Lys Thr Asn Asn
        195                 200                 205
```

Asp Lys Thr Lys Gly Ala Asp Glu Leu Glu Lys Leu Phe Glu Ser Val
210                 215                 220

Lys Asn Leu Ser Lys Ala Ala Lys Glu Met Leu Thr Asn Ser Ser Glu
225                 230                 235                 240

Lys Phe Ala Gly Lys Leu Lys Asn Glu His Ala Ser Leu Gly Lys Lys
                245                 250                 255

Asp Ala Thr Asp Asp Ala Lys Lys Ala Ile Leu Lys Thr His Gly
        260                 265                 270

Asn Thr Asp Lys Gly Ala Lys Glu Leu Lys Asp Leu Ser Asp Ser Val
        275                 280                 285

Glu Ser Leu Val Ser Asp Phe Thr Lys Lys Leu Gln Ser Ser His
290                 295                 300

Ala Gln Leu Gly Val Ala Gly Ala Thr Thr Asp Glu Glu Ala Lys
305                 310                 315                 320

Lys Ala Ile Leu Arg Thr Asn Ala Ile Lys Asp Lys Gly Ala Asp Glu
                325                 330                 335

Leu Glu Lys Leu Phe Lys Ser Val Glu Ser Leu Ala Lys Ala Ala Gln
                340                 345                 350

Asp Ala Leu Ala Asn Ser Val Asn Glu Leu Thr Ser Lys Lys Leu Lys
                355                 360                 365

Glu Lys His Thr Asp Leu Gly Lys Lys Asp Ala Thr Asp Val His Ala
370                 375                 380

Lys Glu Ala Ile Leu Lys Thr Asn Gly Thr Lys Asp Lys Gly Ala Ala
385                 390                 395                 400

Glu Leu Glu Lys Leu Phe Glu Ser Val Glu Asn Leu Ala Lys Ala Ala
                405                 410                 415

Lys Glu Met Leu Ser Asn Ser Asn Lys Ala Phe Thr Lys Leu Lys
                420                 425                 430

Ser Ser His Ala Glu Leu Gly Ile Ala Asn Gly Ala Ala Thr Asp Ala
                435                 440                 445

Asn Ala Lys Ala Ala Ile Leu Lys Thr Asn Gly Thr Lys Asp Lys Gly
        450                 455                 460

Ala Gln Glu Leu Glu Lys Leu Phe Glu Ser Val Lys Asn Leu Ser Lys
465                 470                 475                 480

Ala Ala Gln Glu Thr Leu Asn Asn Ser Ser Glu Ser Phe Thr Lys Lys
                485                 490                 495

Leu Ser Asp Asn Gln Ala Glu Leu Gly Ile Glu Asn Ala Thr Asp Asp
                500                 505                 510

Asn Ala Lys Lys Ala Ile Leu Lys Thr His Asn Ala Lys Asp Lys Gly
        515                 520                 525

Ala Glu Glu Leu Val Lys Leu Ser Glu Ser Val Ala Gly Leu Leu Lys
530                 535                 540

Ala Ala Gln Ala Ile Leu Ala Asn Ser Val Lys Glu Leu Thr Ser Pro
545                 550                 555                 560

Val Val Ala Glu Ser Pro Lys Lys Pro
                565

<210> SEQ ID NO 66
<211> LENGTH: 503
<212> TYPE: PRT
<213> ORGANISM: Artificial
<220> FEATURE:
<223> OTHER INFORMATION: synthetic chimeric polypeptide

<400> SEQUENCE: 66

```
Ser Glu Lys Phe Thr Thr Lys Leu Lys Asp Ser His Ala Glu Leu Gly
1               5                   10                  15

Ile Gln Ser Val Gln Asp Asn Ala Lys Lys Ala Ile Leu Lys Thr
            20                  25                  30

His Gly Thr Lys Asp Lys Gly Ala Lys Glu Leu Glu Glu Leu Phe Lys
            35                  40                  45

Ser Leu Glu Ser Leu Ser Lys Ala Ala Gln Ala Ala Leu Thr Asn Ser
50                  55                  60

Val Lys Glu Leu Thr Asn Ser Asp Lys Phe Thr Lys Lys Leu Thr Asp
65                  70                  75                  80

Ser His Ala Gln Leu Gly Ala Val Gly Ala Ile Asn Asp Asp Arg
                85                  90                  95

Ala Lys Glu Ala Ile Leu Lys Thr His Gly Thr Asn Asp Lys Gly Ala
                100                 105                 110

Lys Glu Leu Lys Glu Leu Ser Glu Ser Val Glu Ser Leu Ala Lys Ala
                115                 120                 125

Ala Gln Ala Ala Leu Ala Asn Ser Ser Glu Ala Phe Thr Lys Lys Leu
            130                 135                 140

Lys Asp Ser Asn Ala Gln Leu Gly Met Gln Asn Gly Ala Ala Thr Asp
145                 150                 155                 160

Ala His Ala Lys Ala Ala Ile Leu Lys Thr Asp Ala Thr Lys Asp Lys
                165                 170                 175

Gly Ala Thr Glu Leu Gly Glu Leu Phe Lys Ser Val Glu Ser Leu Ser
            180                 185                 190

Lys Ala Ala Gln Glu Ala Ser Val Ala Phe Thr Ser Lys Leu Lys Ser
            195                 200                 205

Ser Asn Ala Gln Leu Gly Val Ala Asn Gly Asn Ala Thr Asp Asp Asp
210                 215                 220

Ala Lys Lys Ala Ile Leu Lys Thr Asn Thr Pro Asn Asp Lys Gly Ala
225                 230                 235                 240

Lys Glu Leu Lys Glu Leu Phe Glu Ser Val Glu Ser Leu Ala Lys Ala
                245                 250                 255

Ala Gln Ala Ala Leu Val Asn Ser Val Gln Glu Leu Thr Asn Ser Glu
            260                 265                 270

Ala Phe Thr Asn Arg Leu Lys Gly Ser His Ala Gln Leu Gly Val Ala
            275                 280                 285

Ala Ala Thr Asp Asp His Ala Lys Glu Ala Ile Leu Lys Ser Asn Pro
            290                 295                 300

Thr Lys Asp Lys Gly Ala Lys Glu Leu Lys Asp Leu Ser Glu Ser Val
305                 310                 315                 320

Glu Ser Leu Ala Lys Ala Ala Gln Glu Ala Leu Ala Asn Ser Val Lys
                325                 330                 335

Glu Leu Thr Asn Ser Glu Ala Phe Thr Lys Lys Leu Lys Asp Asn Asn
                340                 345                 350

Ala Gln Leu Gly Ile Gln Asn Val Gln Asp Val Glu Ala Lys Lys Ala
            355                 360                 365

Ile Leu Lys Thr Asn Gly Asp Ile Ser Lys Ser Glu Ala Phe Thr Asn
            370                 375                 380

Lys Leu Lys Glu Lys His Ala Glu Leu Gly Val Asn Gly Gly Asp Thr
385                 390                 395                 400

Thr Asp Asp Asn Ala Lys Ala Ala Ile Phe Lys Thr His Pro Thr Lys
                405                 410                 415
```

-continued

```
Asp Lys Gly Val Glu Asp Leu Glu Lys Leu Ser Glu Ser Val Lys Ser
            420                 425                 430

Leu Leu Lys Ala Ala Gln Ala Ala Leu Ser Asn Ser Ala Ala Phe Thr
        435                 440                 445

Lys Lys Leu Gln Asp Gly His Val Asp Leu Gly Lys Thr Asp Val Thr
    450                 455                 460

Asp Asp Asn Ala Lys Glu Ala Ile Leu Lys Thr Asn Pro Thr Lys Thr
465                 470                 475                 480

Lys Gly Ala Thr Glu Leu Glu Glu Leu Phe Lys Ser Val Glu Gly Leu
                485                 490                 495

Val Lys Ala Ala Lys Glu Ala
            500
```

<210> SEQ ID NO 67
<211> LENGTH: 512
<212> TYPE: PRT
<213> ORGANISM: Artificial
<220> FEATURE:
<223> OTHER INFORMATION: synthetic chimeric polypeptide

<400> SEQUENCE: 67

```
Ser Glu Glu Phe Thr Asn Lys Leu Lys Ser Gly His Ala Asp Leu Gly
1               5                   10                  15

Lys Gln Asp Ala Thr Asp His Ala Lys Ala Ile Leu Lys Thr
            20                  25                  30

His Ala Thr Thr Asp Lys Gly Ala Lys Glu Phe Lys Asp Leu Phe Glu
        35                  40                  45

Ser Val Glu Gly Leu Leu Lys Ala Ala Gln Val Ala Leu Thr Asn Ser
    50                  55                  60

Val Lys Glu Leu Thr Ser Lys Leu Lys Gly Gly His Ala Glu Leu Gly
65                  70                  75                  80

Leu Ala Ala Ala Thr Asp Glu Asn Ala Lys Lys Ala Ile Leu Lys Thr
                85                  90                  95

Asn Gly Thr Lys Asp Lys Gly Ala Glu Glu Leu Glu Lys Leu Phe Lys
            100                 105                 110

Ser Val Glu Ser Leu Ala Lys Ala Ala Lys Glu Ser Leu Thr Asn Ser
        115                 120                 125

Val Lys Glu Leu Thr Asn Thr Lys Leu Arg Asp Ser His Ala Glu Leu
    130                 135                 140

Gly Ile Gln Asn Val Gln Asp Asn Ala Lys Arg Ala Ile Leu Lys
145                 150                 155                 160

Thr His Gly Asn Lys Asp Lys Gly Ala Lys Glu Leu Lys Glu Leu Ser
                165                 170                 175

Glu Ser Leu Glu Lys Leu Ser Lys Ala Ala Gln Ala Ala Leu Ala Asn
            180                 185                 190

Ser Val Gln Glu Leu Thr Ser Ser Glu Ala Phe Thr Asn Lys Leu Lys
        195                 200                 205

Glu Lys Thr Gln Glu Leu Ala Val Ala Gly Ala Ala Thr Asp Ile
    210                 215                 220

Asp Ala Lys Lys Ala Ile Leu Lys Thr Asn Arg Asp Lys Asp Leu Gly
225                 230                 235                 240

Ala Asp Glu Arg Gly Lys Leu Phe Lys Ser Val Glu Ser Leu Ser Lys
                245                 250                 255

Ala Ala Gln Glu Ala Ser Ala Asn Ser Val Lys Glu Leu Thr Ser Ser
            260                 265                 270
```

Glu Ala Phe Thr Asp Lys Leu Lys Asn Glu His Ala Ser Leu Gly Lys
                275                 280                 285

Lys Asp Ala Thr Asp Asp Ala Lys Lys Ala Ile Leu Lys Thr Asn
    290                 295                 300

Val Asp Lys Thr Lys Gly Ala Asp Glu Leu Ile Lys Leu Ser Gly Ser
305                 310                 315                 320

Leu Glu Ser Leu Ser Lys Ala Ala Gln Ala Ile Leu Ala Asn Ser Glu
                325                 330                 335

Ala Phe Thr Lys Lys Leu Gln Asp Ser Asn Ala Asp Leu Gly Lys His
                340                 345                 350

Asn Ala Thr Asp Ala Asp Ser Lys Glu Ala Ile Leu Lys Thr Asn Gly
                355                 360                 365

Thr Lys Thr Lys Gly Ala Lys Glu Leu Glu Glu Leu Phe Lys Ser Val
    370                 375                 380

Glu Ser Leu Ser Lys Ala Ala Lys Glu Ala Leu Ser Asn Ser Val Lys
385                 390                 395                 400

Glu Leu Thr Ser Ser Gln Asp Phe Ile Asn Lys Leu Lys Gly Gly His
                405                 410                 415

Ala Glu Leu Gly Leu Val Ala Ala Thr Asp Ala Asn Ala Lys Ala Ala
                420                 425                 430

Ile Leu Lys Thr Asn Gly Asp Lys Thr Lys Gly Ala Asp Glu Phe Glu
                435                 440                 445

Lys Leu Phe Lys Ser Val Glu Gly Leu Leu Lys Ala Ala Gln Glu Ala
                450                 455                 460

Leu Thr Asn Ser Val Lys Glu Leu Thr Ser Ser Glu Ala Phe Thr Lys
465                 470                 475                 480

Lys Leu Gln Asp Ser Asn Ala Asp Leu Gly Lys His Asp Ala Thr Asp
                485                 490                 495

Ala Asp Ala Lys Lys Ala Ile Leu Lys Thr Asp Ala Thr Lys Asp Lys
                500                 505                 510

<210> SEQ ID NO 68
<211> LENGTH: 431
<212> TYPE: PRT
<213> ORGANISM: Artificial
<220> FEATURE:
<223> OTHER INFORMATION: synthetic chimeric polypeptide

<400> SEQUENCE: 68

Ser Glu Thr Phe Thr Asn Lys Leu Lys Glu Lys His Thr Asp Leu Gly
1               5                   10                  15

Lys Glu Gly Val Thr Lys Gly Ala Glu Glu Leu Gly Lys Leu Phe Glu
                20                  25                  30

Ser Val Glu Val Leu Ser Lys Ala Ala Lys Glu Met Leu Ala Asn Ser
            35                  40                  45

Val Lys Glu Leu Thr Ser Ser Glu Glu Phe Ser Thr Lys Leu Lys Asp
    50                  55                  60

Asn His Ala Gln Leu Gly Ile Gln Gly Val Thr Lys Gly Val Glu Glu
65                  70                  75                  80

Leu Glu Lys Leu Ser Gly Ser Leu Glu Ser Leu Ser Ser Glu Asp Phe
                85                  90                  95

Thr Lys Lys Leu Glu Gly Glu His Ala Gln Leu Gly Ile Glu Asn Val
                100                 105                 110

Thr Ala Ala Glu Leu Glu Lys Leu Phe Lys Ala Val Glu Asn Leu Ala
                115                 120                 125

Lys Ala Ala Lys Glu Met Ala Lys Leu Lys Gly Glu His Thr Asp Leu
            130                 135                 140

Gly Lys Glu Gly Val Thr Lys Gly Ala Asp Glu Leu Glu Lys Leu Phe
145                 150                 155                 160

Glu Ser Val Lys Asn Leu Ser Lys Ala Ala Lys Glu Met Leu Thr Asn
                165                 170                 175

Ser Lys Glu Ser Glu Lys Phe Ala Gly Lys Leu Lys Asn Glu His Ala
            180                 185                 190

Ser Leu Gly Lys Lys Asp Ala Thr Lys Gly Ala Lys Glu Leu Lys Asp
            195                 200                 205

Leu Ser Asp Ser Val Glu Ser Leu Val Lys Ala Ser Asp Asp Phe Thr
210                 215                 220

Lys Lys Leu Gln Ser Ser His Ala Gln Leu Gly Val Ala Gly Gly Ala
225                 230                 235                 240

Thr Thr Ala Asp Glu Leu Glu Lys Leu Phe Lys Ser Val Glu Ser Leu
                245                 250                 255

Ala Lys Ala Ala Gln Asp Ala Leu Ala Asn Ser Val Asn Glu Leu Thr
            260                 265                 270

Ser Lys Lys Leu Lys Glu Lys His Thr Asp Leu Gly Lys Lys Asp Ala
            275                 280                 285

Thr Ala Ala Glu Leu Glu Lys Leu Phe Glu Ser Val Glu Asn Leu Ala
290                 295                 300

Lys Ala Ala Lys Glu Met Leu Ser Asn Ser Asn Lys Ala Phe Thr Asp
305                 310                 315                 320

Lys Leu Lys Ser Ser His Ala Glu Leu Gly Ile Ala Asn Gly Ala Ala
                325                 330                 335

Thr Lys Gly Ala Gln Glu Leu Glu Lys Leu Phe Glu Ser Val Lys Asn
            340                 345                 350

Leu Ser Lys Ala Ala Gln Glu Thr Leu Asn Asn Ser Val Lys Glu Ser
            355                 360                 365

Glu Ser Phe Thr Lys Lys Leu Ser Asp Asn Gln Ala Glu Leu Gly Ile
370                 375                 380

Glu Asn Ala Thr Lys Gly Ala Glu Glu Leu Val Lys Leu Ser Glu Ser
385                 390                 395                 400

Val Ala Gly Leu Leu Lys Ala Ala Gln Ala Ile Leu Ala Asn Ser Val
                405                 410                 415

Lys Glu Leu Thr Ser Pro Val Val Ala Glu Ser Pro Lys Lys Pro
            420                 425                 430

<210> SEQ ID NO 69
<211> LENGTH: 381
<212> TYPE: PRT
<213> ORGANISM: Artificial
<220> FEATURE:
<223> OTHER INFORMATION: synthetic chimeric polypeptide

<400> SEQUENCE: 69

Ser Glu Lys Phe Thr Thr Lys Leu Lys Asp Ser His Ala Glu Leu Gly
1               5                   10                  15

Ile Gln Ser Val Gln Asp Lys Gly Ala Lys Glu Leu Glu Glu Leu Phe
            20                  25                  30

Lys Ser Leu Glu Ser Leu Ser Lys Ala Ala Gln Ala Ala Leu Thr Asn
        35                  40                  45

Ser Val Lys Glu Leu Thr Asn Ser Asp Lys Phe Thr Lys Lys Leu Thr
    50                  55                  60

Asp Ser His Ala Gln Leu Gly Ala Val Gly Ala Ile Asn Asp Lys
65                  70                  75                  80

Gly Ala Lys Glu Leu Lys Glu Leu Ser Glu Ser Val Glu Ser Leu Ala
            85                  90                  95

Lys Ala Ala Gln Ala Ala Leu Ala Asn Ser Ser Glu Ala Phe Thr Lys
        100                 105                 110

Lys Leu Lys Asp Ser Asn Ala Gln Leu Gly Met Gln Asn Gly Ala Ala
    115                 120                 125

Thr Asp Lys Gly Ala Thr Glu Leu Gly Glu Leu Phe Lys Ser Val Glu
130                 135                 140

Ser Leu Ser Lys Ala Ala Gln Glu Ala Ser Val Ala Phe Thr Ser Lys
145                 150                 155                 160

Leu Lys Ser Ser Asn Ala Gln Leu Gly Val Ala Asn Gly Asn Ala Thr
                165                 170                 175

Asp Lys Gly Ala Lys Glu Leu Lys Glu Leu Phe Glu Ser Val Glu Ser
            180                 185                 190

Leu Ala Lys Ala Ala Gln Ala Ala Leu Val Asn Ser Val Gln Glu Leu
        195                 200                 205

Thr Asn Ser Glu Ala Phe Thr Asn Arg Leu Lys Gly Ser His Ala Gln
    210                 215                 220

Leu Gly Val Ala Ala Thr Asp Lys Gly Ala Lys Glu Leu Lys Asp
225                 230                 235                 240

Leu Ser Glu Ser Val Glu Ser Leu Ala Lys Ala Ala Gln Glu Ala Leu
                245                 250                 255

Ala Asn Ser Val Lys Glu Leu Thr Asn Ser Glu Ala Phe Thr Lys Lys
            260                 265                 270

Leu Lys Asp Asn Asn Ala Gln Leu Gly Ile Gln Asn Val Gln Ser Glu
        275                 280                 285

Ala Phe Thr Asn Lys Leu Lys Glu Lys His Ala Glu Leu Gly Val Asn
    290                 295                 300

Gly Gly Asp Thr Thr Asp Lys Gly Val Glu Asp Leu Glu Lys Leu Ser
305                 310                 315                 320

Glu Ser Val Lys Ser Leu Leu Lys Ala Ala Gln Ala Ala Leu Ser Asn
                325                 330                 335

Ser Ala Ala Phe Thr Lys Lys Leu Gln Asp Gly His Val Asp Leu Gly
            340                 345                 350

Lys Thr Asp Val Thr Thr Lys Gly Ala Thr Glu Leu Glu Glu Leu Phe
        355                 360                 365

Lys Ser Val Glu Gly Leu Val Lys Ala Ala Lys Glu Ala
    370                 375                 380

<210> SEQ ID NO 70
<211> LENGTH: 383
<212> TYPE: PRT
<213> ORGANISM: Artificial
<220> FEATURE:
<223> OTHER INFORMATION: synthetic chimeric polypeptide

<400> SEQUENCE: 70

Ser Glu Glu Phe Thr Asn Lys Leu Lys Ser Gly His Ala Asp Leu Gly
1               5                   10                  15

Lys Gln Asp Ala Thr Lys Gly Ala Lys Glu Phe Lys Asp Leu Phe Glu
            20                  25                  30

Ser Val Glu Gly Leu Leu Lys Ala Ala Gln Val Ala Leu Thr Asn Ser
        35                  40                  45

Val Lys Glu Leu Thr Ser Lys Leu Lys Gly Gly His Ala Glu Leu Gly
 50                  55                  60

Leu Ala Ala Ala Thr Lys Gly Ala Glu Leu Glu Lys Leu Phe Lys
 65                  70                  75                  80

Ser Val Glu Ser Leu Ala Lys Ala Ala Lys Glu Ser Leu Thr Asn Ser
                 85                  90                  95

Val Lys Glu Leu Thr Asn Thr Lys Leu Arg Asp Ser His Ala Glu Leu
            100                 105                 110

Gly Ile Gln Asn Val Gln Lys Gly Ala Lys Glu Leu Lys Glu Leu Ser
            115                 120                 125

Glu Ser Leu Glu Lys Leu Ser Lys Ala Ala Gln Ala Ala Leu Ala Asn
130                 135                 140

Ser Val Gln Glu Leu Thr Ser Ser Glu Ala Phe Thr Asn Lys Leu Lys
145                 150                 155                 160

Glu Lys Thr Gln Glu Leu Ala Val Ala Ala Gly Ala Ala Thr Leu Gly
                165                 170                 175

Ala Asp Glu Arg Gly Lys Leu Phe Lys Ser Val Glu Ser Leu Ser Lys
            180                 185                 190

Ala Ala Gln Glu Ala Ser Ala Asn Ser Val Lys Glu Leu Thr Ser Ser
            195                 200                 205

Glu Ala Phe Thr Asp Lys Leu Lys Asn Glu His Ala Ser Leu Gly Lys
210                 215                 220

Lys Asp Ala Thr Lys Gly Ala Asp Glu Leu Ile Lys Leu Ser Gly Ser
225                 230                 235                 240

Leu Glu Ser Leu Ser Lys Ala Ala Gln Ala Ile Leu Ala Asn Ser Glu
                245                 250                 255

Ala Phe Thr Lys Lys Leu Gln Asp Ser Asn Ala Asp Leu Gly Lys His
            260                 265                 270

Asn Ala Thr Lys Gly Ala Lys Glu Leu Glu Glu Leu Phe Lys Ser Val
            275                 280                 285

Glu Ser Leu Ser Lys Ala Ala Lys Glu Ala Leu Ser Asn Ser Val Lys
290                 295                 300

Glu Leu Thr Ser Ser Gln Asp Phe Ile Asn Lys Leu Lys Gly Gly His
305                 310                 315                 320

Ala Glu Leu Gly Leu Val Ala Ala Thr Lys Gly Ala Asp Glu Phe Glu
                325                 330                 335

Lys Leu Phe Lys Ser Val Glu Gly Leu Leu Lys Ala Ala Gln Glu Ala
            340                 345                 350

Leu Thr Asn Ser Val Lys Glu Leu Thr Ser Ser Glu Ala Phe Thr Lys
            355                 360                 365

Lys Leu Gln Asp Ser Asn Ala Asp Leu Gly Lys His Asp Ala Thr
370                 375                 380

<210> SEQ ID NO 71
<211> LENGTH: 432
<212> TYPE: PRT
<213> ORGANISM: Artificial
<220> FEATURE:
<223> OTHER INFORMATION: synthetic chimeric polypeptide

<400> SEQUENCE: 71

Ser Glu Thr Phe Thr Asn Lys Leu Lys Glu Lys His Thr Asp Leu Gly
1               5                   10                  15

Lys Glu Gly Val Thr Lys Gly Ala Glu Glu Leu Gly Lys Leu Phe Glu
            20                  25                  30

Ser Val Glu Val Leu Ser Lys Ala Ala Lys Glu Met Leu Ala Asn Ser
            35                  40                  45

Val Lys Glu Leu Thr Ser Lys Gly Val Glu Leu Glu Lys Leu Ser
 50                  55                  60

Gly Ser Leu Glu Ser Leu Ser Asn Lys Ala Phe Thr Asp Lys Leu Lys
 65                  70                  75                  80

Ser Ser His Ala Glu Leu Gly Ile Ala Asn Gly Ala Ala Thr Lys Lys
                 85                  90                  95

Leu Lys Glu Lys His Thr Asp Leu Gly Lys Lys Asp Ala Thr Lys Gly
            100                 105                 110

Ala Asp Glu Leu Glu Lys Leu Phe Glu Ser Val Lys Asn Leu Ser Lys
            115                 120                 125

Ala Ala Lys Glu Met Leu Thr Asn Ser Lys Glu Ile Ala Ala Glu Leu
            130                 135                 140

Glu Lys Leu Phe Lys Ala Val Glu Asn Leu Ala Lys Ala Ala Lys Glu
145                 150                 155                 160

Met Ala Lys Leu Lys Gly Glu His Thr Asp Leu Gly Lys Glu Gly Val
                165                 170                 175

Thr Ser Glu Glu Phe Ser Thr Lys Leu Lys Asp Asn His Ala Gln Leu
            180                 185                 190

Gly Ile Gln Gly Val Thr Lys Gly Ala Lys Glu Leu Lys Asp Leu Ser
            195                 200                 205

Asp Ser Val Glu Ser Leu Val Lys Ala Ala Ala Glu Leu Glu Lys Leu
            210                 215                 220

Phe Glu Ser Val Glu Asn Leu Ala Lys Ala Ala Lys Glu Met Leu Ser
225                 230                 235                 240

Asn Ser Ser Glu Lys Phe Ala Gly Lys Leu Lys Asn Glu His Ala Ser
                245                 250                 255

Leu Gly Lys Lys Asp Ala Thr Ser Glu Asp Phe Thr Lys Lys Leu Glu
            260                 265                 270

Gly Glu His Ala Gln Leu Gly Ile Glu Asn Val Thr Lys Gly Ala Gln
            275                 280                 285

Glu Leu Glu Lys Leu Phe Glu Ser Val Lys Asn Leu Ser Lys Ala Ala
            290                 295                 300

Gln Glu Thr Leu Asn Asn Ser Val Lys Glu Ala Asp Glu Leu Glu Lys
305                 310                 315                 320

Leu Phe Lys Ser Val Glu Ser Leu Ala Lys Ala Gln Asp Ala Leu
                325                 330                 335

Ala Asn Ser Val Asn Glu Leu Thr Ser Ser Glu Ser Phe Thr Lys Lys
            340                 345                 350

Leu Ser Asp Asn Gln Ala Glu Leu Gly Ile Glu Asn Ala Thr Ser Asp
            355                 360                 365

Asp Phe Thr Lys Lys Leu Gln Ser Ser His Ala Gln Leu Gly Val Ala
            370                 375                 380

Gly Gly Ala Thr Thr Lys Gly Ala Glu Glu Leu Val Lys Leu Ser Glu
385                 390                 395                 400

Ser Val Ala Gly Leu Leu Lys Ala Ala Gln Ala Ile Leu Ala Asn Ser
                405                 410                 415

Val Lys Glu Leu Thr Ser Pro Val Val Ala Glu Ser Pro Lys Lys Pro
            420                 425                 430

<210> SEQ ID NO 72
<211> LENGTH: 382
<212> TYPE: PRT

<213> ORGANISM: Artificial
<220> FEATURE:
<223> OTHER INFORMATION: synthetic chimeric polypeptide

<400> SEQUENCE: 72

```
Ser Glu Ala Phe Thr Lys Lys Leu Lys Asp Ser Asn Ala Gln Leu Gly
1               5                   10                  15

Met Gln Asn Gly Ala Ala Thr Asp Lys Gly Ala Lys Glu Leu Glu Glu
            20                  25                  30

Leu Phe Lys Ser Leu Glu Ser Leu Ser Lys Ala Ala Gln Ala Ala Leu
        35                  40                  45

Thr Asn Ser Val Lys Glu Leu Thr Asn Lys Asp Lys Gly Ala Lys Glu
50                  55                  60

Leu Lys Glu Leu Phe Glu Ser Val Glu Ser Leu Ala Lys Ala Ala Gln
65                  70                  75                  80

Ala Ala Leu Val Asn Ser Val Gln Glu Leu Thr Asn Ser Glu Lys Phe
                85                  90                  95

Thr Thr Lys Leu Lys Asp Ser His Ala Glu Leu Gly Ile Gln Ser Val
            100                 105                 110

Gln Ser Asp Lys Phe Thr Lys Lys Leu Thr Asp Ser His Ala Gln Leu
        115                 120                 125

Gly Ala Val Gly Gly Ala Ile Asn Asp Lys Gly Ala Lys Glu Leu Lys
    130                 135                 140

Glu Leu Ser Glu Ser Val Glu Ser Leu Ala Lys Ala Ala Gln Ala Ala
145                 150                 155                 160

Leu Ala Asn Ser Asp Lys Gly Ala Lys Glu Leu Lys Asp Leu Ser Glu
                165                 170                 175

Ser Val Glu Ser Leu Ala Lys Ala Ala Gln Glu Ala Leu Ala Asn Ser
            180                 185                 190

Val Lys Glu Leu Thr Asn Ser Val Ala Phe Thr Ser Lys Leu Lys Ser
        195                 200                 205

Ser Asn Ala Gln Leu Gly Val Ala Asn Gly Asn Ala Thr Ser Glu Ala
    210                 215                 220

Phe Thr Lys Lys Leu Lys Asp Asn Asn Ala Gln Leu Gly Ile Gln Asn
225                 230                 235                 240

Val Gln Thr Lys Gly Ala Thr Glu Leu Glu Glu Leu Phe Lys Ser Val
                245                 250                 255

Glu Gly Leu Val Lys Ala Ala Lys Glu Ala Asp Lys Gly Val Glu Asp
            260                 265                 270

Leu Glu Lys Leu Ser Glu Ser Val Lys Ser Leu Leu Lys Ala Ala Gln
        275                 280                 285

Ala Ala Leu Ser Asn Ser Ala Ala Phe Thr Lys Lys Leu Gln Asp Gly
    290                 295                 300

His Val Asp Leu Gly Lys Thr Asp Val Thr Ser Glu Ala Phe Thr Asn
305                 310                 315                 320

Arg Leu Lys Gly Ser His Ala Gln Leu Gly Val Ala Ala Ala Thr Asp
                325                 330                 335

Lys Gly Ala Thr Glu Leu Gly Glu Leu Phe Lys Ser Val Glu Ser Leu
            340                 345                 350

Ser Lys Ala Ala Gln Glu Ala Ser Glu Ala Phe Thr Asn Lys Leu Lys
        355                 360                 365

Glu Lys His Ala Glu Leu Gly Val Asn Gly Gly Asp Thr Thr
    370                 375                 380
```

-continued

```
<210> SEQ ID NO 73
<211> LENGTH: 383
<212> TYPE: PRT
<213> ORGANISM: Artificial
<220> FEATURE:
<223> OTHER INFORMATION: synthetic chimeric polypeptide

<400> SEQUENCE: 73
```

Ser Glu Glu Phe Thr Asn Lys Leu Lys Ser Gly His Ala Asp Leu Gly
1               5                   10                  15

Lys Gln Asp Ala Thr Lys Gly Ala Glu Phe Lys Asp Leu Phe Glu
            20                  25                  30

Ser Val Glu Gly Leu Leu Lys Ala Ala Gln Val Ala Leu Thr Asn Ser
        35                  40                  45

Val Lys Glu Leu Thr Ser Lys Glu Lys Gly Ala Glu Leu Glu Lys
    50                  55                  60

Leu Phe Lys Ser Val Glu Ser Leu Ala Lys Ala Ala Lys Glu Ser Leu
65                  70                  75                  80

Thr Asn Ser Val Lys Glu Leu Thr Asn Ser Glu Ala Phe Thr Asp Lys
                85                  90                  95

Leu Lys Asn Glu His Ala Ser Leu Gly Lys Lys Asp Ala Thr Lys
            100                 105                 110

Leu Arg Asp Ser His Ala Glu Leu Gly Ile Gln Asn Val Gln Leu Gly
        115                 120                 125

Ala Asp Glu Arg Gly Lys Leu Phe Lys Ser Val Glu Ser Leu Ser Lys
    130                 135                 140

Ala Ala Gln Glu Ala Ser Ala Asn Ser Val Lys Glu Leu Thr Ser Lys
145                 150                 155                 160

Glu Lys Gly Ala Lys Glu Leu Glu Glu Leu Phe Lys Ser Val Glu Ser
                165                 170                 175

Leu Ser Lys Ala Ala Lys Glu Ala Leu Ser Asn Ser Val Lys Glu Leu
            180                 185                 190

Thr Ser Ser Glu Ala Phe Thr Lys Lys Leu Gln Asp Ser Asn Ala Asp
        195                 200                 205

Leu Gly Lys His Asn Ala Thr Ser Glu Ala Phe Thr Lys Lys Leu Gln
    210                 215                 220

Asp Ser Asn Ala Asp Leu Gly Lys His Asp Ala Thr Lys Gly Ala Asp
225                 230                 235                 240

Glu Phe Glu Lys Leu Phe Lys Ser Val Glu Gly Leu Leu Lys Ala Ala
                245                 250                 255

Gln Glu Ala Leu Thr Asn Ser Val Lys Glu Leu Thr Ser Glu Leu Lys
            260                 265                 270

Glu Leu Ser Glu Ser Leu Glu Lys Leu Ser Lys Ala Ala Gln Ala Ala
        275                 280                 285

Leu Ala Asn Ser Val Gln Glu Leu Thr Ser Ser Glu Ala Phe Thr Asn
    290                 295                 300

Lys Leu Lys Glu Lys Thr Gln Glu Leu Ala Val Ala Ala Gly Ala Ala
305                 310                 315                 320

Thr Lys Leu Lys Gly Gly His Ala Glu Leu Gly Leu Ala Ala Ala Thr
                325                 330                 335

Lys Gly Ala Asp Glu Leu Ile Lys Leu Ser Gly Ser Leu Glu Ser Leu
            340                 345                 350

Ser Lys Ala Ala Gln Ala Ile Leu Ala Asn Ser Gln Asp Phe Ile Asn
        355                 360                 365

Lys Leu Lys Gly Gly His Ala Glu Leu Gly Leu Val Ala Ala Thr
    370                 375                 380

<210> SEQ ID NO 74
<211> LENGTH: 257
<212> TYPE: PRT
<213> ORGANISM: Borrelia burgdorferi

<400> SEQUENCE: 74

Cys Lys Gln Asn Val Ser Ser Leu Asp Glu Lys Asn Ser Val Ser Val
1               5                   10                  15
Asp Leu Pro Gly Glu Met Lys Val Leu Val Ser Lys Glu Lys Asn Lys
            20                  25                  30
Asp Gly Lys Tyr Asp Leu Ile Ala Thr Val Asp Lys Leu Glu Leu Lys
        35                  40                  45
Gly Thr Ser Asp Lys Asn Asn Gly Ser Gly Val Leu Glu Gly Val Lys
    50                  55                  60
Ala Asp Lys Ser Lys Val Lys Leu Thr Ile Ser Asp Asp Leu Gly Gln
65                  70                  75                  80
Thr Thr Leu Glu Val Phe Lys Glu Asp Gly Lys Thr Leu Val Ser Lys
                85                  90                  95
Lys Val Thr Ser Lys Asp Lys Ser Ser Thr Glu Glu Lys Phe Asn Glu
            100                 105                 110
Lys Gly Glu Val Ser Glu Lys Ile Ile Thr Arg Ala Asp Gly Thr Arg
        115                 120                 125
Leu Glu Tyr Thr Gly Ile Lys Ser Asp Gly Ser Gly Lys Ala Lys Glu
    130                 135                 140
Val Leu Lys Gly Tyr Val Leu Glu Gly Thr Leu Thr Ala Glu Lys Thr
145                 150                 155                 160
Thr Leu Val Val Lys Glu Gly Thr Val Thr Leu Ser Lys Asn Ile Ser
                165                 170                 175
Lys Ser Gly Glu Val Ser Val Glu Leu Asn Asp Thr Asp Ser Ser Ala
            180                 185                 190
Ala Thr Lys Lys Thr Ala Ala Trp Asn Ser Gly Thr Ser Thr Leu Thr
        195                 200                 205
Ile Thr Val Asn Ser Lys Lys Thr Lys Asp Leu Val Phe Thr Lys Glu
    210                 215                 220
Asn Thr Ile Thr Val Gln Gln Tyr Asp Ser Asn Gly Thr Lys Leu Glu
225                 230                 235                 240
Gly Ser Ala Val Glu Ile Thr Lys Leu Asp Glu Ile Lys Asn Ala Leu
                245                 250                 255
Lys

<210> SEQ ID NO 75
<211> LENGTH: 257
<212> TYPE: PRT
<213> ORGANISM: Borrelia burgdorferi

<400> SEQUENCE: 75

Cys Lys Gln Asn Val Ser Ser Leu Asp Glu Lys Asn Ser Val Ser Val
1               5                   10                  15
Asp Leu Pro Gly Glu Met Asn Val Leu Val Ser Lys Glu Lys Asn Lys
            20                  25                  30
Asp Gly Lys Tyr Asp Leu Ile Ala Thr Val Asp Lys Leu Glu Leu Lys
        35                  40                  45
Gly Thr Ser Asp Lys Asn Asn Gly Ser Gly Val Leu Glu Gly Val Lys
    50                  55                  60

Ala Asp Lys Ser Lys Val Lys Leu Thr Ile Ser Asp Asp Leu Gly Gln
65                  70                  75                  80

Thr Thr Leu Glu Val Phe Lys Glu Asp Gly Lys Thr Leu Val Ser Lys
                85                  90                  95

Lys Val Thr Ser Lys Asp Lys Ser Ser Thr Glu Glu Lys Phe Asn Glu
                100                 105                 110

Lys Gly Glu Val Ser Glu Lys Ile Ile Thr Arg Ala Asp Gly Thr Arg
                115                 120                 125

Leu Glu Tyr Thr Glu Ile Lys Ser Asp Gly Ser Gly Lys Ala Lys Glu
            130                 135                 140

Val Leu Lys Gly Tyr Val Leu Glu Gly Thr Leu Thr Ala Glu Lys Thr
145                 150                 155                 160

Thr Leu Val Val Lys Glu Gly Thr Val Thr Leu Ser Lys Asn Ile Ser
                165                 170                 175

Lys Ser Gly Glu Val Ser Val Glu Leu Asn Asp Thr Asp Ser Ser Ala
                180                 185                 190

Ala Thr Lys Lys Thr Ala Ala Trp Asn Ser Gly Thr Ser Thr Leu Thr
            195                 200                 205

Ile Thr Val Asn Ser Lys Lys Thr Lys Asp Leu Val Phe Thr Lys Glu
            210                 215                 220

Asn Thr Ile Thr Val Gln Gln Tyr Asp Ser Asn Gly Thr Lys Leu Glu
225                 230                 235                 240

Gly Ser Ala Val Glu Ile Thr Lys Leu Asp Glu Ile Lys Asn Ala Leu
                245                 250                 255

Lys

<210> SEQ ID NO 76
<211> LENGTH: 257
<212> TYPE: PRT
<213> ORGANISM: Borrelia burgdorferi

<400> SEQUENCE: 76

Cys Lys Gln Asn Val Ser Ser Leu Asp Glu Lys Asn Ser Val Ser Val
1               5                   10                  15

Asp Leu Pro Gly Glu Met Lys Val Leu Val Ser Lys Glu Lys Asn Lys
                20                  25                  30

Asp Gly Lys Tyr Asp Leu Ile Ala Thr Val Asp Lys Leu Glu Leu Lys
            35                  40                  45

Gly Thr Ser Asp Lys Asn Asn Gly Ser Gly Val Leu Glu Gly Val Lys
        50                  55                  60

Ala Asp Lys Ser Lys Val Lys Leu Thr Ile Ser Asp Asp Leu Gly Gln
65                  70                  75                  80

Thr Thr Leu Glu Val Phe Lys Glu Asp Gly Lys Thr Leu Val Ser Lys
                85                  90                  95

Lys Val Thr Ser Lys Asp Lys Ser Ser Thr Glu Glu Lys Phe Asn Glu
                100                 105                 110

Lys Gly Glu Val Ser Glu Lys Ile Ile Thr Arg Ala Asp Gly Thr Arg
                115                 120                 125

Leu Glu Tyr Thr Glu Ile Lys Ser Asp Gly Ser Gly Lys Ala Lys Glu
            130                 135                 140

Val Leu Lys Gly Tyr Val Leu Glu Gly Thr Leu Thr Ala Glu Lys Thr
145                 150                 155                 160

Thr Leu Val Val Lys Glu Gly Thr Val Thr Leu Ser Lys Asn Ile Ser
                165                 170                 175

-continued

```
Lys Ser Gly Glu Val Ser Val Glu Leu Asn Asp Thr Asp Ser Ser Ala
            180             185                 190

Ala Thr Lys Lys Thr Ala Ala Trp Asn Ser Gly Thr Ser Thr Leu Thr
        195                 200                 205

Ile Thr Val Asn Ser Lys Lys Thr Lys Asp Leu Val Phe Thr Lys Glu
    210                 215                 220

Asn Thr Ile Thr Val Gln Gln Tyr Asp Ser Asn Gly Thr Lys Leu Glu
225                 230                 235                 240

Gly Ser Ala Val Glu Ile Thr Lys Leu Asp Glu Ile Lys Asn Ala Leu
                245                 250                 255

Lys
```